United States Patent
Ishikawa et al.

(10) Patent No.: US 9,096,632 B2
(45) Date of Patent: Aug. 4, 2015

(54) MODULATOR OF ACTIVITY OF ADENYLATE CYCLASE

(75) Inventors: Yoshihiro Ishikawa, Yokohama (JP); Satoshi Okumura, Yokohama (JP); Yujiro Hoshino, Yokohama (JP); Seiichi Inoue, Yokohama (JP)

(73) Assignee: Public University Corporation Yokohama City University, Kanagawa (JP)

( * ) Notice: Subject to any disclaimer, the term of this patent is extended or adjusted under 35 U.S.C. 154(b) by 0 days.

(21) Appl. No.: 13/880,346

(22) PCT Filed: Oct. 20, 2011

(86) PCT No.: PCT/JP2011/074098
§ 371 (c)(1),
(2), (4) Date: Jun. 5, 2013

(87) PCT Pub. No.: WO2012/056976
PCT Pub. Date: May 3, 2012

(65) Prior Publication Data
US 2013/0261073 A1 Oct. 3, 2013

(30) Foreign Application Priority Data
Oct. 27, 2010 (JP) .................... 2010-240301

(51) Int. Cl.
A01N 43/04 (2006.01)
A61K 31/70 (2006.01)
C07H 19/06 (2006.01)
A61K 31/7064 (2006.01)
A61K 31/7056 (2006.01)
A61K 31/706 (2006.01)
A61K 31/7052 (2006.01)
A61K 31/7042 (2006.01)
A61K 31/7076 (2006.01)
C07H 19/19 (2006.01)
A23L 1/30 (2006.01)

(52) U.S. Cl.
CPC . *C07H 19/06* (2013.01); *A23L 1/30* (2013.01); *A61K 31/706* (2013.01); *A61K 31/7042* (2013.01); *A61K 31/7052* (2013.01); *A61K 31/7056* (2013.01); *A61K 31/7064* (2013.01); *A61K 31/7076* (2013.01); *C07H 19/19* (2013.01)

(58) Field of Classification Search
None
See application file for complete search history.

(56) References Cited

FOREIGN PATENT DOCUMENTS

| CN | 1817866 A | 8/2006 |
|---|---|---|
| JP | 2000-302675 | 10/2000 |
| WO | WO-9518636 A2 | 7/1995 |
| WO | WO 20071112348 A2 | 10/2007 |

OTHER PUBLICATIONS

Hakimelahi et al. Helvetica Chimica Acta (1987), vol. 70, pp. 219-231.*
Sperling et al. Alzheimer's & Dementia (2011), vol. 7, pp. 280-292.*
Bruce M. Chassy et al., "Binding and Hydrolysis of 2- and 6-Substituted Purine Ribonucleosides and 9-Substituted Adenine Necleosides", Journal of Biological Chemistry, 1967, vol. 242, No. 16, pp. 3655-3658.
Ivan Rychlik et al., Substrate Specificity of Ribosomal Peptidyl Trasferase: 2'(3')-O-Aminoacyl Nucleosides as Acceptors of the Peptide Chain on the Amino Acid Site, J. Mol. Biol., 1969, vol. 43, No. 1, pp. 13-24.
K. Chung et al., "Template-Directed Organic Synthesis, a Model for the Peptidyl Transfer Reaction of Protein Biosynthesis", Bioorganic Chemistry, 1978, vol. 7, No. 3, pp. 303-312.
Prakash Bhuta et al., "Elongation Factor $T_u$-Ribosome Dependent Guanosine 5'-Triphosphate Hydrolysis: Elucidation . . . ", Biochemistry, 1982, vol. 21, No. 5, pp. 899-905.

(Continued)

*Primary Examiner* — Patrick Lewis
(74) *Attorney, Agent, or Firm* — Morgan, Lewis & Bockius LLP

(57) ABSTRACT

The present invention provides a novel compound capable of inhibiting cardiac adenylyl cyclase.
The present invention relates to a compound represented by the following formula (I) or a pharmaceutically acceptable salt, ester or solvate thereof:

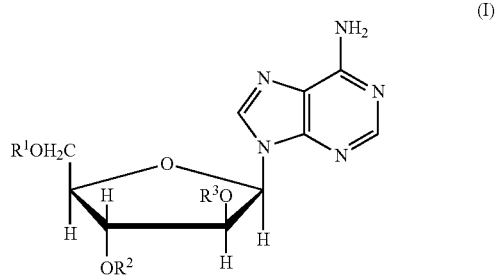

where $R^1$, $R^2$ and $R^3$ each independently represent a hydrogen atom or an acyl group having an acidic or basic substituent, provided that all of $R^1$, $R^2$ and $R^3$ are not simultaneously a hydrogen atom.
The present invention also provides a modulator of adenylyl cyclase activity, a pharmaceutical composition and a food composition, all of which comprise the above-described compound or a pharmaceutically acceptable salt, ester or solvate thereof.

6 Claims, 8 Drawing Sheets

(56) References Cited

OTHER PUBLICATIONS

Max H. Iltzsch et al., "Structure-Activity Relationship for the Binding of Nucleoside Ligands to Adenosine Kinase From *Toxoplasma gondii*", Biochemical Pharmacology, 1995, vol. 49, No. 10, pp. 1501-1512.

Alex M. Aronov et al., "Synthesis and Structure-Activity Relationship of Adenosine Analogs as Inhibitors . . . ,", Bioorganic & Medicinal Chemistry Letters, 1998, vol. 8, No. 24, pp. 3505-3510.

Roger A. Johnson et al., "Cation and Structural Requirements for P Site-Mediated Inhibition of Adenylate Cyclase", Molecular Pharmacology, 1989, vol. 35, No. 5, pp. 681-688.

Takeshi Onda et al., "Type Specific Regulation of Adenylyl Cyclase", Journal of Biological Chemistry, 2001, Vo. 276, No. 51, pp. 47785-47793.

Iwatsubo K et al: "Direct inhibition of type 5 adenylyl cyclase prevents myocardial apoptosis without functional deterioration", Journal of Biological Chemistry, American Society for Biochemistry and Molecular Biology, US, vol. 279, No. 39, Jan. 1, 2004, pp. 40938-40945.

Extended European Search Report dated Feb. 28, 2014 in corresponding European Patent Application No. 11836112.0.

English translation of international preliminary report on patentability dated May 2, 2013 issued in corresponding PCT application PCT/JP2011/074098.

\* cited by examiner

AC5 Inhibitor (15mg/kg/day 7days)

Time to death induced by strychnine n=4-10,
<0.01; *P<0.001, +++P<0.001 vs CTRL; ##P<0.01 vs Vidarabine 0.525 mmol/kg

Esophageal pacing

MODULATOR OF ACTIVITY OF ADENYLATE CYCLASE

TECHNICAL FIELD

The present invention relates to a modulator of adenylyl cyclase activity.

BACKGROUND ART

Heart failure is a major cause of death throughout the world. In Japan, heart failure is one of the three major causes of death. A worldwide standard guideline for treating heart failure is to inhibit the chronically enhanced sympathetic nervous system activity in heart failure patients and renin-angiotensin system inhibitors and β-adrenoreceptor antagonists (β-blockers) are used as main therapeutics. However, transient inhibition of cardiac function by β-blockers is a big obstacle to introduction of the treatment for patients, especially for aged patients. On the other hand, β-blockers also have an inhibitory action on the respiratory tract and this causes a serious problem in aged patients who often have complications such as pulmonary emphysema. β-adrenoreceptors modulate cardiac function by increasing the concentration of intracellular cyclic AMP (cAMP) through activation of adenylyl cyclase enzyme present in the cell membrane. Briefly, the above-mentioned β-blockers exert their pharmacological effects by inhibiting the activity of adenylyl cyclase enzyme and the downstream cAMP signals. On the other hand, since β-adrenoreceptors are also expressed in the pulmonary bronchus, β-blockers cause bronchial smooth muscle contraction, which induces abnormalities in respiratory function.

Such adverse effects of β-blockers on the respiratory system may be explained by the fact that having only 3 subtypes, β-adrenoreceptors are relatively low in the organ specificity of their expression. On the other hand, adenylyl cyclase is known to have 9 subtypes and the subtypes called cardiac are expressed specifically in the heart but little in the lung. β-blockers classified as agents of class II in Vaughan Williams classification have long been known to have an anti-arrhythmic action. Therefore, by selectively inhibiting cardiac adenylyl cyclase, therapeutic effects on heart failure and arrhythmia which are similar to the effects of β-blockers might be exerted without causing adverse effects on the respiratory tract.

Some drugs targeting cardiac adenylyl cyclase have already been applied clinically (Non-Patent Document No. 1). Although some compounds have already been reported as cardiac adenylyl cyclase inhibitors (Non-Patent Documents Nos. 2 and 3), neither clinical application has started nor novel compounds have been reported. Animal experiments performed to date have strongly suggested that cardiac adenylyl cyclase inhibitors are potentially useful as therapeutics for heart failure (Non-Patent Documents Nos. 4 to 7).

PRIOR ART LITERATURE

Non-Patent Documents

Non-Patent Document No. 1: Toya et al., J. Mol. Cell. Cardiol. 1998 January; 30(0:97-108
Non-Patent Document No. 2: J. Biol. Chem. 276; 47785-47793, 2001
Non-Patent Document No. 3: J. Biol. Chem. 279; 40938-40945, 2004
Non-Patent Document No. 4: Circ. Res. 93: 364-371, 2003
Non-Patent Document No. 5: Proc. Natl. Acad. Sci. USA. 100:9986-90, 2003
Non-Patent Document No. 6: Cell 130:247-58, 2007
Non-Patent Document No. 7: Circulation 116:1776-83, 2007

DISCLOSURE OF THE INVENTION

Problem for Solution by the Invention

It is an object of the present invention to provide a novel compound which has not been reported yet and is capable of inhibiting cardiac adenylyl cyclase.

Means to Solve the Problem

The present inventors have synthesized a plurality of derivatives from vidarabine, a known inhibitor of cardiac adenylyl cyclase, and examined their inhibitory actions on cardiac adenylyl cyclase and their prophylactic effects on heart failure. With respect to prophylactic effect on heart failure, heart failure was actually produced in mouse models, which were then administered with cardiac adenylyl cyclase inhibitors and compared to study their therapeutic effects. As a result, the present inventors found novel compounds capable of inhibiting cardiac adenylyl cyclase, whereby the present invention has been achieved.

A summary of the present invention is as described below.

(1) A compound represented by the following formula (I) or a pharmaceutically acceptable salt, ester or solvate thereof:

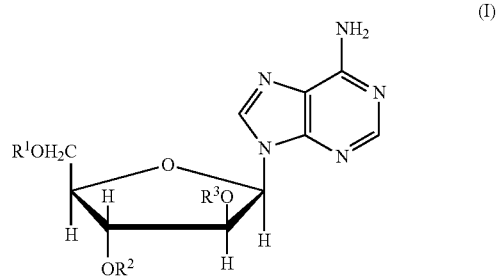

(I)

where $R^1$, $R^2$ and $R^3$ each independently represent a hydrogen atom or an acyl group having an acidic or basic substituent, provided that all of $R^1$, $R^2$ and $R^3$ are not simultaneously a hydrogen atom.

(2) The compound of (1) above, wherein the acyl group having an acidic or basic substituent is represented by the following formula:

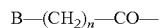

B—(CH$_2$)$_n$—CO— where n represents an integer from 1 to 4 and B is an acidic or basic substituent.

(3) The compound of (1) or (2) above, wherein the acidic or basic substituent is an optionally alkyl-substituted amino group, a carboxyl group, or a hydroxycarbamoyl group.

(4) The compound of any one of (1) to (3) above, which is represented by any of the following formulas:

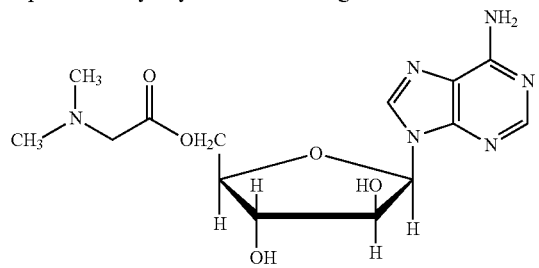

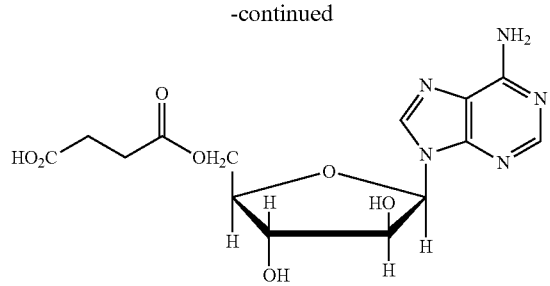

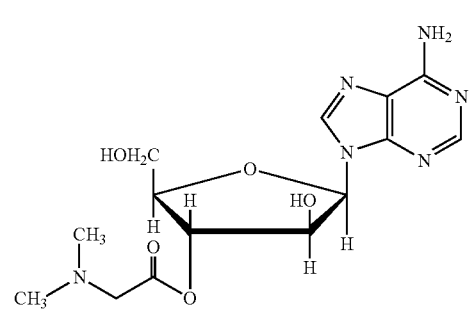

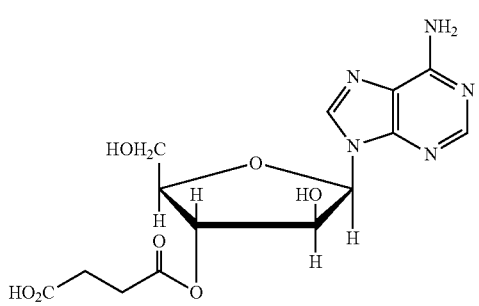

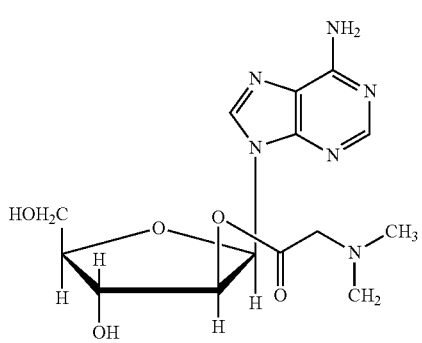

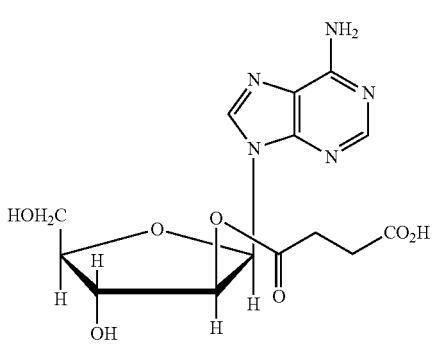

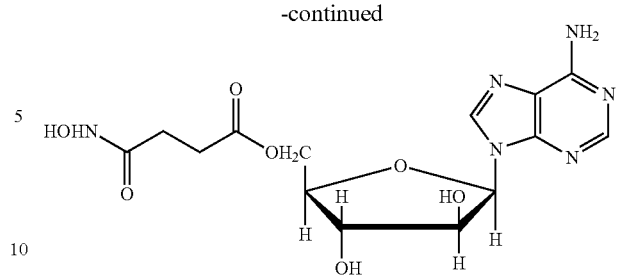

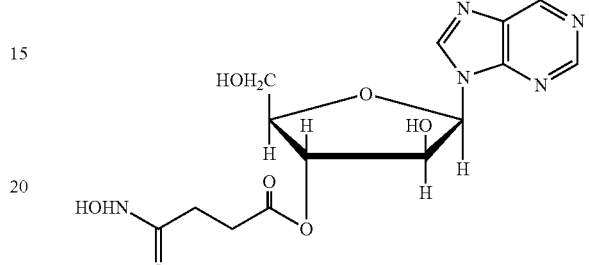

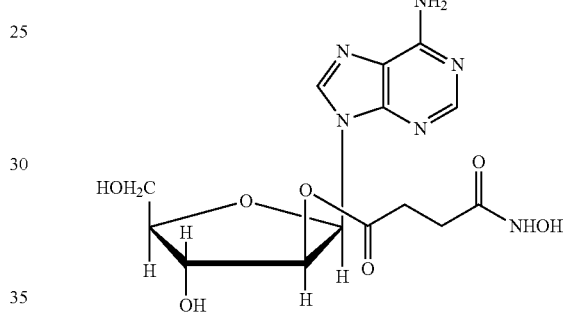

(5) A modulator of adenylyl cyclase activity, comprising the compound of any one of (1) to (4) above or a pharmaceutically acceptable salt, ester or solvate thereof.
(6) The modulator of (5), wherein the adenylyl cyclase is cardiac adenylyl cyclase.
(7) A pharmaceutical composition comprising the compound of any one of (1) to (4) above or a pharmaceutically acceptable salt, ester or solvate thereof.
(8) The pharmaceutical composition of (7) above, which is for use in prevention and/or treatment of an indication for β-blockers,
(9) The pharmaceutical composition of (8) above, wherein the indication for β-blockers is selected from the group consisting of heart failure, myocardial infarction, arrhythmia, angina, hypertension, and conditions and diseases associated therewith.
(10) A food composition comprising the compound of any one of (1) to (4) above or a pharmaceutically acceptable salt, ester or solvate thereof.
(11) The food composition of (10) above, which is used for antiaging and extending life span, for prevention of diseases and conditions associated therewith, or for health maintenance.
(12) A method of preventing and/or treating an indication for β-blockers, comprising administering to a subject a pharmaceutically effective amount of the compound of any one of (1) to (4) above or a pharmaceutically acceptable salt, ester or solvate thereof.
(13) Use of the compound of any one of (1) to (4) above or a pharmaceutically acceptable salt, ester or solvate thereof, for preventing and/or treating an indication for β-blockers.

(14) The compound of any one of (1) to (4) above or a pharmaceutically acceptable salt, ester or solvate thereof, for use in a method of preventing and/or treating an indication for β-blockers.

(15) A method of antiaging and extgending life span, prevention of diseases and conditions associated therewith or health maintenance, comprising administering to a subject a pharmaceutically effective amount of the compound of any one of (1) to (4) above or a pharmaceutically acceptable salt, ester or solvate thereof.

(16) Use of the compound of any one of (1) to (4) above or a pharmaceutically acceptable salt, ester or solvate thereof, for anti-aging and extending life span, prevention of diseases and conditions associated therewith or health maintenance.

(17) The compound of any one of (1) to (4) above or a pharmaceutically acceptable salt, ester or solvate thereof, for use in a method of anti-aging and extending life span, prevention of diseases and conditions associated therewith or health maintenance.

Although vidarabine has an inhibitory effect on cardiac adenylyl cyclase, biodistribution of vidarabine shows extensive migration to central nervous system tissues because of its poor water solubility. For this reason, vidarabine may exhibit adverse effects on the central nervous system. Since the novel compound of the present invention has extremely high water solubility, its migration to the central nervous system is extremely small, indicating that it is believed that a high therapeutic effect on the heart can be obtained.

Effect of the Invention

The novel compound of the present invention is effective as an inhibitor of the activity of cardiac adenylyl cyclase. It is possible to use the novel compound of the present invention as a therapeutic for diseases such as heart failure, myocardial infarction and arrhythmia.

The present specification encompasses the contents disclosed in the specification and/or drawings of Japanese Patent Application No. 2010-240301 based on which the present patent application claims priority.

BEST MODES FOR CARRYING OUT THE INVENTION

Figure 1:
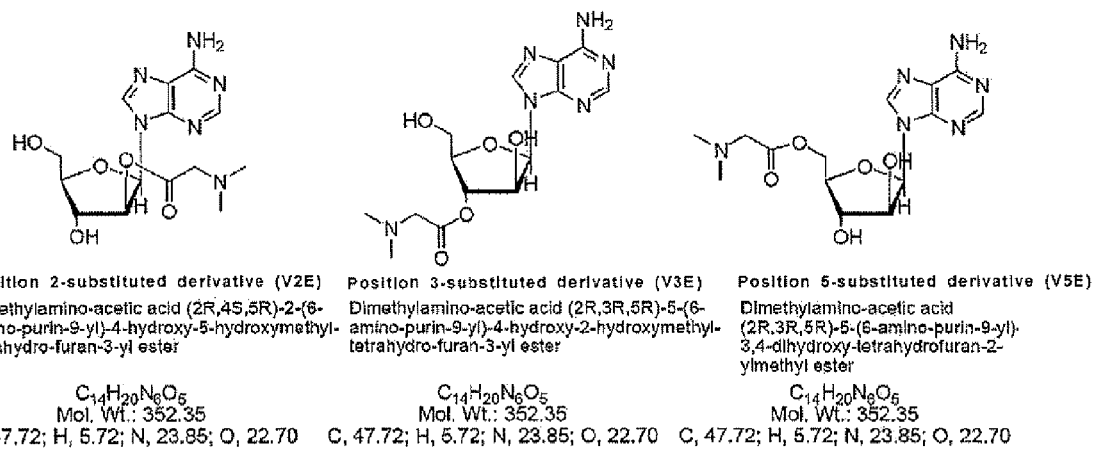
FIG. 1 Chemical structures of vidarabine derivatives as novel compounds

Hereinbelow, embodiments of the present invention will be described in more detail.

The present invention provides a compound represented by the following formula (I) and a pharmaceutically acceptable salt, ester or solvate thereof.

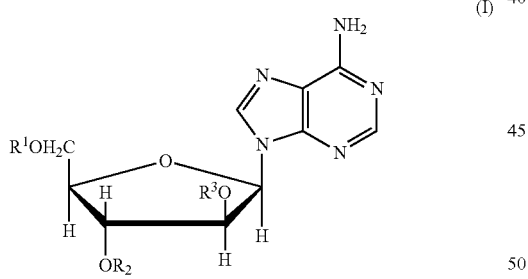

where $R^1$, $R^2$ and $R^3$ each independently represent a hydrogen atom or an acyl group having an acidic or basic substituent, provided that all of $R^1$, $R^2$ and $R^3$ are not simultaneously a hydrogen atom.

The compound of the present invention may occur as stereoisomers, and the present invention encompasses all of these stereoisomers. For example, optically active substances, diastereomers, racemates and the like are all included in the present invention.

In the present invention, the acyl group having an acidic or basic substituent may be a group represented by the formula B—$(CH_2)_n$—CO— where n represents an integer from 1 to 4 and B is an acidic or basic substituent.

The acidic or basic substituent represented by B may be an optionally alkyl substituted amino group, a carboxyl group or a hydroxycarbamoyl group. The alkyl group as an optional substitutent on the amino group is a $C_{1-4}$ straight- or branched-chain alkyl group. Preferable alkyl groups include, but are not limited to, methyl group, ethyl group, n-propyl group, isopropyl group, n-butyl group, isobutyl group, sec-butyl group and tert-butyl group.

The compound of the present invention may be exemplified by compounds represented by any of the following formulas.

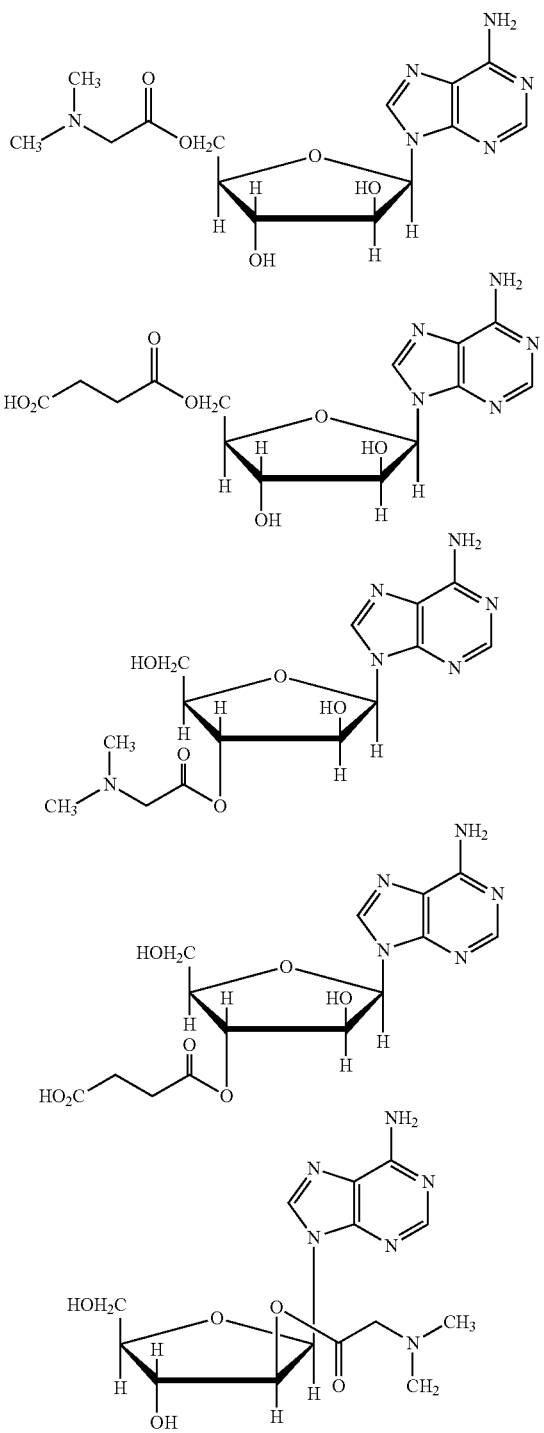

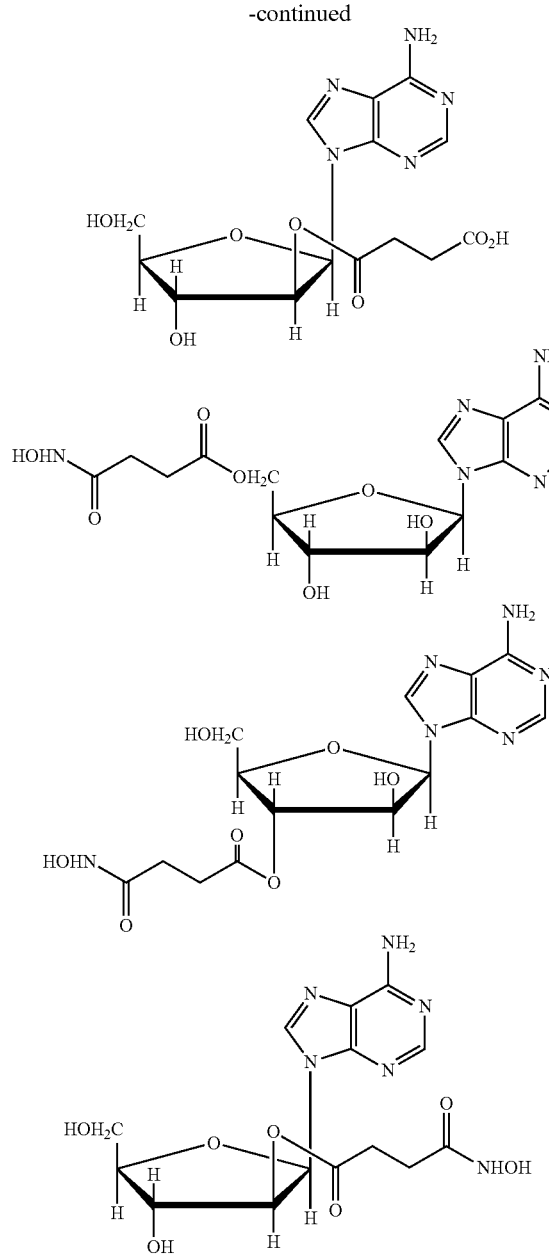

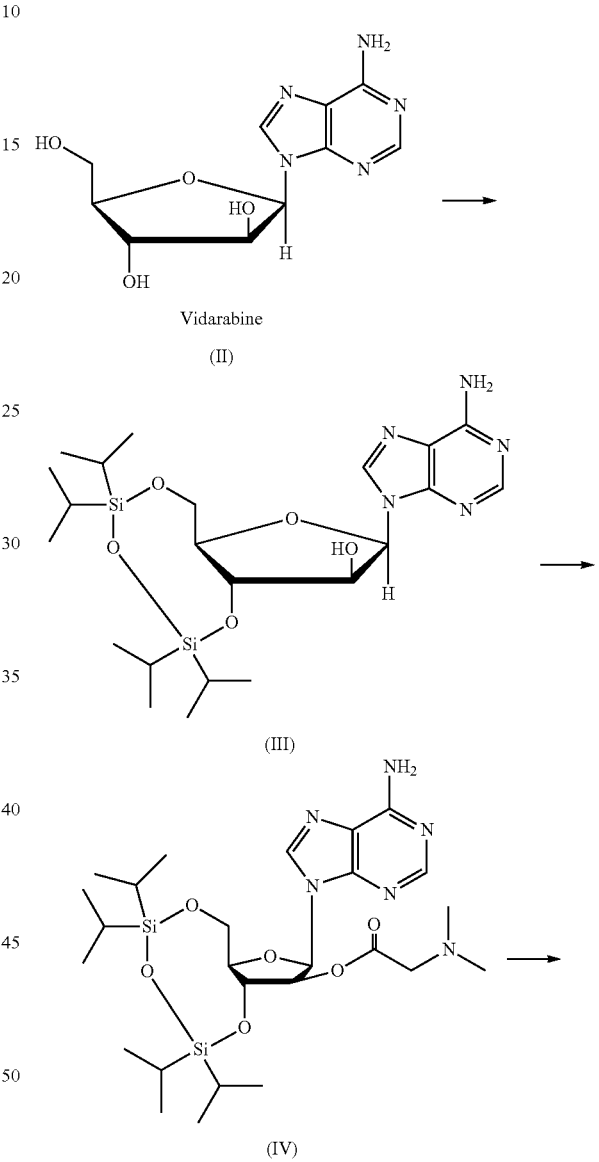

The compound of the present invention may be prepared according to the following reaction schemes.

According to a previously disclosed method (O'Mahony, G; Sundgren, A.; Svensson, S.; Grotli, M. Tetrahedron 2007, 63, 6901-6908), disiloxanylidene-protected compound (III) was synthesized from vidarabine (II). By treating the compound (III) and N,N-dimethylglycine with a dehydration-condensation agent (DCC), it is possible to obtain esterified compound (V) at a high yield. Finally, by treating with tetrabutylammonium fluoride to remove disiloxanylidene group, position 2-substituted derivative (Ia) of interest is obtained. Further, by treating the compound (III) with succinic anhydride, esterified compound (V) is obtained. This esterified compound (V) is activated with 1-propylphosphoric acid cyclic anhydride and treated with hydroxylamine hydrochloride to thereby synthesize hydroxamic acid (VI). Finally, by treating (V) and (VI) separately with tetrabutylammonium fluoride to remove disiloxanylidene group, position 2-substituted derivatives (Ib) and (Ic) of interest are obtained, respectively. Alternatively, instead of N,N-dimethylglycine, carboxylic acid with other acidic or basic group may be used and, instead of succinic anhydride, other carboxylic anhydride may be used.

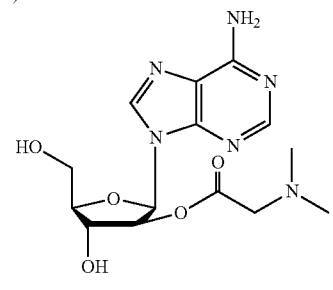

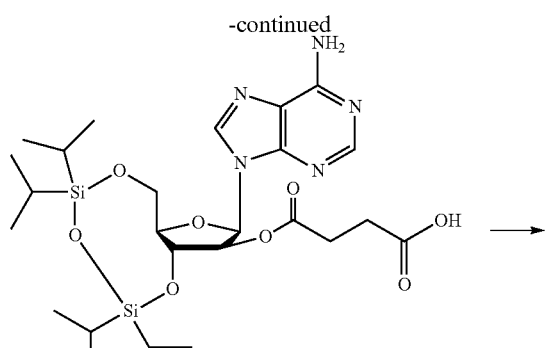

(V)

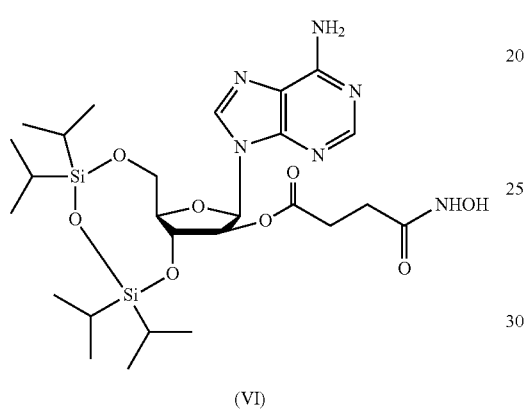

(VI)

(V) or (VI) →

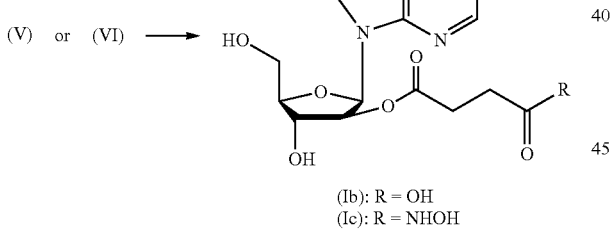

(Ib): R = OH
(Ic): R = NHOH

Based on a previously disclosed method (Shen, W.; Kim, J.-S.; Kish, P. E.; Zhang, J.; Mitchell, S.; Gentry, B. G.; Breitenbach, J. M.; Drach, J. C.; Hilfinger, J. Bio. Med. Chem. Lett. 2009, 19, 792-796), silyl-protected compound (VII) was synthesized from vidarabine (II). By treating the compound (VII) and N,N-dimethylglycine with a dehydration-condensation agent (DCC), it is possible to obtain esterified compound (VIII) at a high yield. Finally, by treating with tetrabutylammonium fluoride to remove silyl group, position 3-substituted derivative (Id) of interest is obtained. Further, by treating the compound (VII) with succinic anhydride, esterified compound (IX) is obtained at a high yield. This esterified compound (IX) is activated with 1-propylphosphoric acid cyclic anhydride and treated with hydroxylamine hydrochloride to thereby synthesize hydroxamic acid (X). Finally, by treating (IX) and (X) separately with tetrabutylammonium fluoride to remove silyl group, position 3-substituted derivatives (Ie) and (If) of interest are obtained, respectively. Alternatively, instead of N,N-dimethylglycine, carboxylic acid with other acidic or basic group may be used and, instead of succinic anhydride, other carboxylic anhydride may be used.

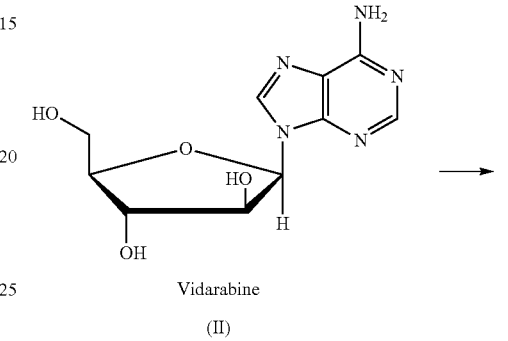

Vidarabine
(II)

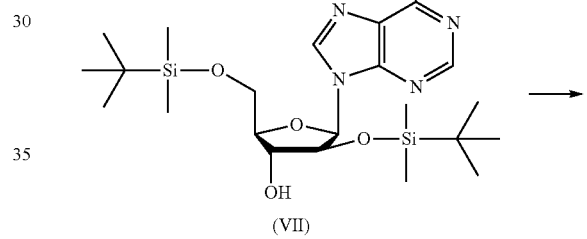

(VII)

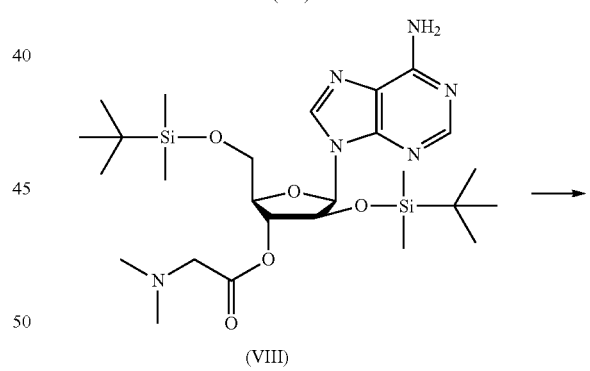

(VIII)

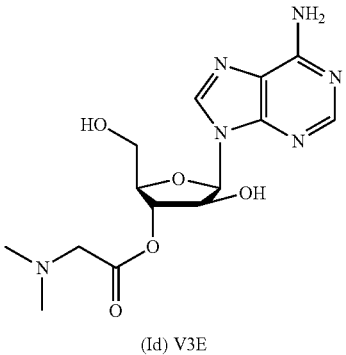

(Id) V3E

-continued (VII) →

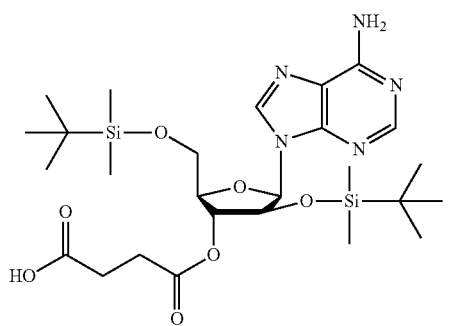

(IX)

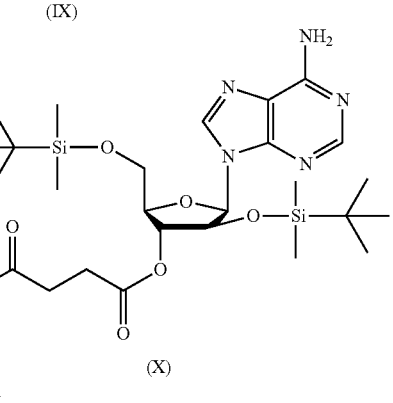

(X)

(IX) or (X) →

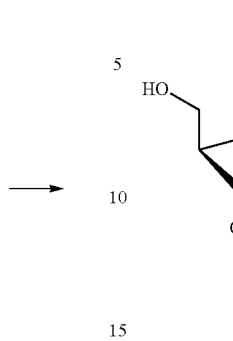

(Ie): R = OH
(If): R = NHOH

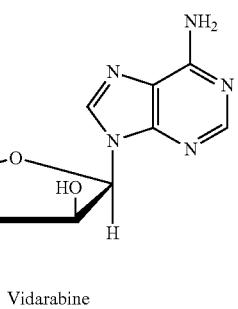

Vidarabine
(II)

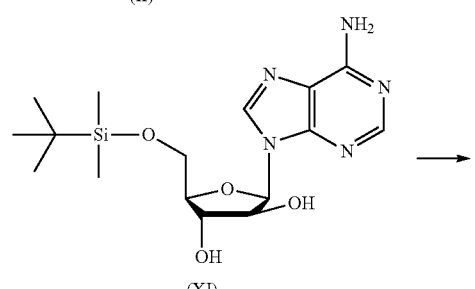

(XI)

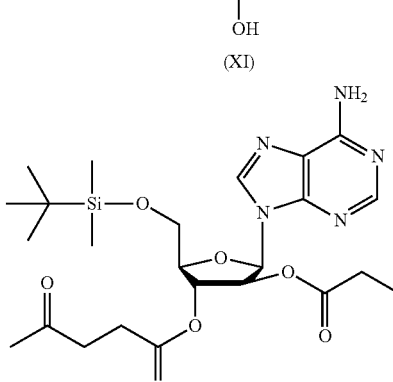

(XII)

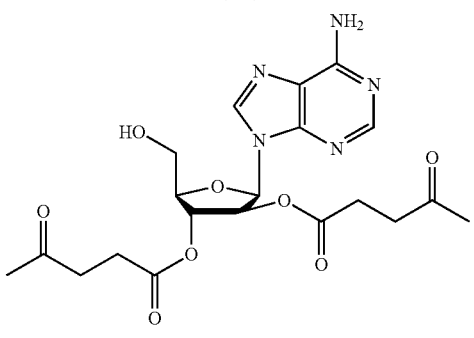

(XIII)

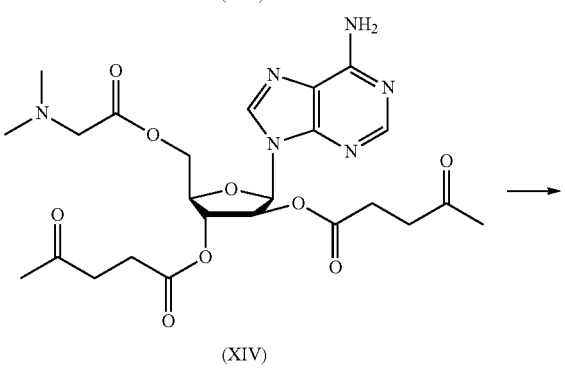

(XIV)

Based on a previously disclosed method (Shen, W.; Kim, J.-S.; Kish, R E.; Zhang, J.; Mitchell, S.; Gentry, B. G.; Breitenbach, J, M.; Drach, J. C.; Hilfinger, J. Bio. Med, Chem. Lett. 2009, 19, 792-796), diester compound (XIII) was synthesized from vidarabine (II). By treating the compound (XIII) and N,N-dimethylglycine with a dehydration-condensation agent (DCC), it is possible to obtain triesterified compound (XIV) at a high yield. Finally, by treating with hydrazine hydrate for deprotection, position 5-substituted derivative (Ig) of interest is obtained. Further, by treating the compound (XIII) with succinic anhydride, esterified compound (XV) is obtained at a high yield. This esterified compound (XV) is activated with 1-propylphosphoric acid cyclic anhydride and treated with hydroxylamine hydrochloride to thereby synthesize hydroxamic acid (XVI). Finally, by treating (XV) and (XVI) separately with hydrazine hydrate for deprotection, position 5-substituted derivatives (Ih) and (Ii) of interest are obtained, respectively. Alternatively, instead of N,N-dimethylglycine, carboxylic acid with other acidic or basic group may be used and, instead of succinic anhydride, other carboxylic anhydride may be used.

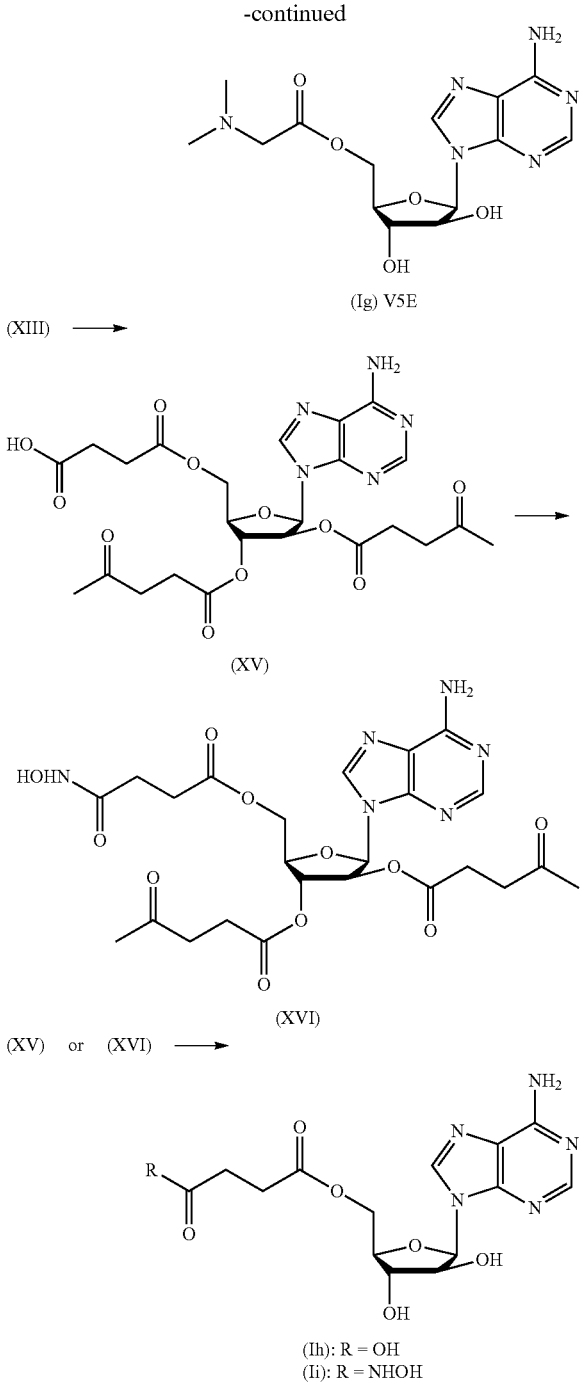

(Ig) V5E (XV)

(XVI)

(Ih): R = OH
(Ii): R = NHOH

Specific examples of pharmaceutically acceptable salts of the compound of the present invention include, but are not limited to, sodium phosphates, sodium salts, potassium salts, hydrochlorides and sulfates. Specific examples of pharmaceutically acceptable esters of the compound of the present invention include, but are not limited to, ethylene glycol esters, diethylene glycol esters, triethylene glycol esters, polyethylene glycol esters and phosphates.

Specific examples of pharmaceutically acceptable solvates of the compound of the present invention include, but are not limited to, solvates with water, methanol, ethanol, dimethylformamide and ethyl acetate.

The compound of the present invention or a pharmaceutically acceptable salt, ester or solvate thereof may be used as a modulator of adenylyl cyclase activity.

Further, the compound of the present invention or a pharmaceutically acceptable salt, ester or solvate thereof may be used for prevention and/or treatment of indications for β-blockers (for example, heart failure, myocardial infarction, arrhythmia, angina, hypertension, and conditions and diseases associated therewith (such as tremor, motion sickness, jet lag, sleep disorder, Basedow's disease, gastroesophageal varices, migraine, Parkinson's disease, etc.)) (Cardiac Practice 20, 69-73, 2009).

Specific examples of conditions and diseases associated with heart failure and/or myocardial infarction include, but are not limited to, arrhythmia, edema, shortness of breath, and angina.

Accordingly, the present invention provides a modulator of adenylyl cyclase activity, comprising the compound represented by the above-described formula (I) or a pharmaceutically acceptable salt, ester or solvate thereof. The drug of the present invention is especially effective on cardiac adenylyl cyclase.

Further, the present invention provides a pharmaceutical composition comprising the compound represented by the above-described formula (I) or a pharmaceutically acceptable salt, ester or solvate thereof.

When the compound of the present invention or a pharmaceutically acceptable salt, ester or solvate thereof is to be used as a medicine, the compound or the like may be formulated into a pharmaceutical preparation (such as injection, capsule, tablet, powder or granule) according to conventional methods and then administered to a subject (human or animal). For example, such a pharmaceutical preparation may be administered orally or parenterally at a daily dose of about 10-50 mg/kg body weight, preferably about 10-15 mg/kg body weight, as calculated for the amount of active ingredient. This dose may be administered either at a time or in several divided portions. However, the dose and frequency of administration may be appropriately changed depending on the symptoms and age of the patient, the administration route, and so forth. When the compound or the like is formulated into injections, a carrier such as distilled water or physiological saline may be used. When the compound or the like is formulated into capsules, tablets, powder or granules, excipients such as starch, lactose, sucrose or calcium carbonate; binders such as starch paste, gum arabic, gelatin, sodium alginate, carboxymethylcellulose or hydroxypropylcellulose; lubricants such as magnesium stearate or talc; and disintegrants such as starch, agar, microcrystalline cellulose, calcium carbonate, sodium hydrogencarbonate or sodium alginate may be used. The content of the active ingredient in pharmaceutical preparations may be varied between 1 to 99% by weight. For example, when the pharmaceutical preparation takes the form of tablets, capsules, granules or powder, the content of the active ingredient is preferably 5-80% by weight; when the pharmaceutical preparation takes the form of injection, the content of the active ingredient is preferably 1-10% by weight.

The compound of the present invention or a pharmaceutically acceptable salt, ester or solvate thereof may also be used for antiaging and extending life span, for prevention of diseases and conditions associated therewith (for example, osteoporosis, aging such as wrinkles in the skin, excessive oxidative stress, hypofunction in organs, etc.) or for health maintenance. For these purposes, the compound of the present invention or a pharmaceutically acceptable salt, ester or solvate thereof may be added to eatables and drinkables (for example, drinks such as sodas; foods such as candies, gum, bread; powdered products such as powder soup, fish flour); or may be combined with appropriate excipients, flavoring agents, coloring agents or the like, and formulated into pills, granules, tablets or capsules. The resultant products may be supplied as health foods or dietary supplements. Thus, the present invention provides a food composition comprising the compound of the present invention or a pharmaceutically acceptable salt, ester or solvate thereof.

The content of the compound of the present invention or a pharmaceutically acceptable salt, ester or solvate thereof in the food composition is preferably 0.1-50% by weight (as calculated for the amount of active ingredient).

EXAMPLES

Hereinbelow, the present invention will be described in more detail with reference to the following Example. However, the present invention is not limited to this Example.

Example 1

In the preceding studies performed by the laboratory of the present inventors, animal models deficient in type 5 adenylyl cyclase (cardiac subtype) were created (Circ. Res. 93: 364-371, 2003; Proc. Natl. Acad. Sci. USA. 100: 9986-90, 2003; Cell 130: 247-58, 2007; Circulation 116:1776-83, 2007). Analyses of these animal models revealed that, although response to catecholamine stimulation decreased, cardiac function in the steady state did not decrease and that they were prevented from a decrease in cardiac function that might be caused by chronic pressure overload and catecholamine stress (Circ. Res. 93: 364-371, 2003; Proc. Natl. Acad. Sci. USA, 100: 9986-90, 2003; Circulation 116:1776-83, 2007). These results indicate that selective inhibition of type 5 works in a heart-protective manner during heart failure without decreasing cardiac function. On the other hand, it has been revealed that a drug (vidarabine) which has been long used clinically as an antiherpes agent has an inhibitory effect selective for type 5; this drug's cardio-protective effect was also revealed in heart failure model experiments (J. Biol. Chem. 279; 40938-40945, 2004). Further, as a result of analyses of 850,000 drugs with an independently developed computer model, a plurality of type 5-selective inhibitors have been identified. On the other hand, in the striatal tissue of the brain of type 5 deficient mice, adenylyl cyclase activity was lowered to about 20% of the activity level in wild type mice (J. Biol. Chem. 278:16936-16940, 2003). Briefly, since the greater part of the adenylyl cyclase activity in wild type striatal tissue is derived from subtype 5, this tissue was believed to be appropriate for use in screening for drugs which selectively inhibit the activity of subtype 5.

The ultimate goal of the present study is to develop a new therapeutic for heart failure that is selective for type 5 adenylyl cyclase. In the present invention, three vidarabine-based compounds were newly synthesized by imparting high levels of hydrophilicity. Further, the inhibitory effects of those compounds on type 5 were examined by the experiments described below. The inventors believe that the increased hydrophilicity contributes to inhibiting the irritancy that might be exerted on type 5 which is expressed in a part of the central nervous system (striatum).

Methods
<Vidarabine Derivatives>

Novel compounds having a dimethylamino acetate group introduced into positions 2, 3 and 5, respectively, of vidarabine were synthesized (FIG. 1).

Synthesis of 2-O—(N,N-Dimethylglycyl)Vidarabine

According to a previously disclosed method (O'Mahony, G; Sundgren, A.; Svensson, S.; Grotli, M. Tetrahedron 2007, 63, 6901-6908), hydroxyl group of vidarabine manufactured by Tokyo Chemical Industry Co., Ltd. was protected with disiloxanylidene group, and compound (III) was prepared.

Compound (III) (510 mg) and N,N-dimethylglycine (113 mg) were dissolved in dichloromethane (5 ml). Dicyclohexylcarbodiimide (DCC) (248 mg) was added thereto, and the solution was agitated for 6 hours at room temperature. Water was added to the reaction mixture. Extraction operation was performed 3 times using dichloromethane. The extracted organic layer was dried over sodium sulfate, followed by filtration. The filtrate was concentrated to obtain a crude product, which was purified by silica gel column chromatography (dichloromethane/methanol 19:1) to thereby obtain 488 mg of compound (IV) (yield 82%). The thus obtained compound (IV) was dissolved in tetrahydrofuran (5 ml). Tetrabutylammonium fluoride (1.8 ml) (1 M tetrahydrofuran solution) was added thereto. The resultant solution was agitated for 12 hours at room temperature. The reaction mixture was concentrated and then purified by silica gel column chromatography (dichloromethane/methanol 15:1) to thereby obtain 260 mg of the compound of interest (Ia) as a white powder (yield 90%).

$^1$H NMR (300 MHz, DMSO-$d_6$)

δ8.24 (s, 1H), 8.11 (s, 1H), 7.29 (s, 2H), 6.45 (d, J=6.0 Hz, 1H), 5.84 (d, J=5.5 Hz, 1H), 5.32 (t, J=6.0 Hz, 1H), 5.12 (t, J=5.7 Hz, 1H), 4.46 (q, J=5.8 Hz, 1H), 3.87-3.61 (m, 3H), 3.05 (d, J=17.0 Hz, 1H), 2.53 (d, J=17.2 Hz, 1H), 1.91 (s, 6H).

Synthesis of 3-O—(N,N-Dimethylglycyl)Vidarabine

Based on a previously disclosed method (Shen, W.; Kim, J.-S.; Kish, P. E.; Zhang, J.; Mitchell, S.; Gentry, B. G.; Breitenbach, J. M.; Drach, J. C.; Hilfinger, J. Bio. Med. Chem. Lett. 2009, 19, 792-796), two hydroxyl groups of vidarabine manufactured by Tokyo Chemical Industry Co., Ltd. were protected with silyl group. Vidarabine (II) (2.0 g) was suspended in N,N-didmethylformamide (20 ml) by agitation. N,N-dimethylaminopyridine (0.114 g) and triethylamine (3.10 ml) were added to the suspension. Finally, tert-butyldimethylchlorosilane (2.26 g) was added thereto. After reacting for 24 hours at room temperature, the solvent was distilled off under reduced pressure. Ethyl acetate was added to the residue. Then, the residue was washed with saturated aqueous ammonium chloride solution and with water and saturated brine. The resultant organic layer was dried over sodium sulfate, and the solvent was distilled off under reduced pressure. As a result, compound (VII) was obtained.

Compound (VII) (496 mg) and N,N-dimethylglycine (113 mg) were dissolved in dichloromethane (5 ml). Dicyclohexylcarbodiimide (DCC) (248 mg) was added thereto, and the solution was agitated for 6 hours at room temperature. Water was added to the reaction mixture. Extraction operation was performed 3 times using dichloromethane. The extracted organic layer was dried over sodium sulfate, followed by filtration. The filtrate was concentrated to obtain a crude product, which was purified by silica gel column chromatography (dichloromethane/methanol 19:1) to thereby obtain 465 mg of compound (VIII) (yield 80%). The thus obtained compound was dissolved in tetrahydrofuran (5 ml). Tetrabutylammonium fluoride (1.8 ml) (1 M tetrahydrofuran solution) was added thereto. The resultant solution was agitated for 12 hours at room temperature. The reaction mixture was concentrated and then purified by silica gel column chromatography (dichloromethane/methanol 15:1) to thereby obtain 259 mg of the compound of interest (Id) (yield 92%).

$^1$H NMR (300 MHz, DMSO-$d_6$)

δ8.22 (s, 1H), 8.14 (s, 1H), 7.30 (s, 2H), 6.27 (d, J=4.4 Hz, 1H), 6.07 (s, 1H), 5.28 (t, J=3.3 Hz, 1H), 5.22 (s, 1H), 4.31 (s, 1H), 4.00-3.96 (m, 1H), 3.70 (s, 2H), 3.29 (s, 2H), 2.28 (s, 6H).

Synthesis of 5-O—(N,N-Dimethylglycyl)Vidarabine

Based on a previously disclosed method (Shen, W.; Kim, J.-S.; Kish, P. E.; Zhang, J.; Mitchell, S.; Gentry, B. G; Breitenbach, J. M.; Drach, J. C.; HiWinger, J. Bio. Med. Chem. Lett. 2009, 19, 792-796), hydroxyl group of vidarabine manufactured by Tokyo Chemical Industry Co., Ltd. was protected with silyl group. Then, vidarabine was condensed with levulinic acid for esterification. Finally, silyl group was removed to thereby prepare compound (XIII).

Compound (XIII) (463 mg) and N,N-dimethylglycine (113 mg) were dissolved in dichloromethane (5 ml). Dicyclohexylcarbodiimide (DCC) (248 mg) was added thereto, and the solution was agitated for 6 hours at room temperature. Water was added to the reaction mixture. Extraction operation was performed 3 times using dichloromethane. The extracted organic layer was dried over sodium sulfate, followed by filtration. The filtrate was concentrated to obtain a crude product, which was purified by silica gel column chromatography (dichloromethane/methanol 19:1) to thereby obtain 400 mg of compound (XIV) (yield 73%). The thus obtained compound was dissolved in pyridine-acetate buffer, to which hydrazine monohydrate (0.107 ml) was added. The resultant solution was agitated for 1 hour at room temperature. The reaction mixture was concentrated and then purified by silica gel column chromatography (dichloromethane/methanol 15:1) to thereby obtain 167 mg of the compound of interest (Ig) as white powder (yield 65%).

$^1$H NMR (300 MHz, DMSO-$d_6$)

δ8.14 (s, 2H), 7.26 (s, 2H), 6.30 (d, J=4.1 Hz, 1H), 5.79 (d, J=4.4 Hz, 1H), 5.72 (d, J=4.1 Hz, 1H), 4.41 (dd, J=7.1, 11.8 Hz, 1H), 4.30 (dd, J=3.6, 11.8 Hz, 1H), 4.16 (s, 2H), 3.98 (s, 1H), 3.19 (d, J=2.8 Hz, 2H), 2.23 (s, 6H).

The thus synthesized position 2-substituted derivative (V2E), position 3-substituted derivative (V3E) and position 5-substituted derivative (V5E) were dissolved in pure water to give a concentration of 10 mM, to thereby prepare stock solutions. Vidarabine was dissolved in 100% dimethylsulfoxide to thereby prepare a 10 mM stock solution.

Synthesis of 2-O-(3-Carboxypropionyl)Vidarabine and 2-O-(3-(N-Hydroxycarbamoyl)Propionyl)Vidarabine According to a previously disclosed method (O'Mahony, G.; Sundgren, A.; Svensson, S.; Grotli, M. Tetrahedron 2007, 63, 6901-6908), hydroxyl group of vidarabine manufactured by Tokyo Chemical Industry Co., Ltd. was protected with disiloxanylidene group, and compound (III) was prepared.

Compound (III) (510 mg) was dissolved in pyridine (5 ml). Succinic anhydride (120 mg) was added thereto and the solution was agitated for 6 hours at room temperature. Water was added to the reaction mixture. Extraction operation was performed 3 times using dichloromethane. The extracted organic layer was dried over sodium sulfate, followed by filtration. The filtrate was concentrated to obtain a crude product, which was purified by silica gel column chromatography (dichloromethane/methanol 19:1) to thereby obtain 580 mg of compound (V) (yield 95%).

1-Propylphosphonic acid cyclic anhydride (1 M ethyl acetate solution; 1 ml) was added to acetonitrile (3 ml). Compound (V) obtained above (610 mg) and triethylamine (0.50 ml) were added thereto. The resultant solution was agitated for 30 minutes at room temperature, followed by addition of hydroxylamine hydrochloride (208 mg). The resultant solution was agitated for 12 hours at room temperature. The reaction mixture was diluted with ethyl acetate, washed with saturated brine and dried over sodium sulfate. Purification by silica gel column chromatography (dichloromethane/methanol 10:1) gave 386 mg of compound (VI) (yield 62%).

Compound (V) (610 mg) or compound (VI) (625 mg) obtained above was dissolved in tetrahydrofuran (5 ml). Tetrabutylammonium fluoride (1 M tetrahydrofuran solution, 3 ml) was added thereto. The resultant solution was agitated for 12 hours at room temperature. The reaction mixture was concentrated and then purified by silica gel column chromatography (dichloromethane/methanol 10:1) to thereby obtain respective compounds of interest, i.e., (Ib) in 302 mg (yield 82%) and (Ic) in 310 mg (yield 81%).

Synthesis of 3-O-(3-Carboxypropionyl)Vidarabine and 3-O-(3-(N-Hydroxycarbamoyl)Propionyl)Vidarabine According to a previously disclosed method (Shen, W.; Kim, J.-S.; Kish, P. E.; Zhang, J.; Mitchell, S.; Gentry, B. G.; Breitenbach, J. M.; Drach, J. C.; Hilfinger, J. Bio. Med. Chem. Lett. 2009, 19, 792-796), hydroxyl group of vidarabine manufactured by Tokyo Chemical Industry Co., Ltd. was protected with silyl group, and compound (VII) was prepared.

Compound (VII) (496 mg) was dissolved in pyridine (5 ml). Succinic anhydride (120 mg) was added thereto and the solution was agitated for 6 hours at room temperature. Water was added to the reaction mixture. Extraction operation was performed 3 times using dichloromethane. The extracted organic layer was dried over sodium sulfate, followed by filtration. The filtrate was concentrated to obtain a crude product, which was purified by silica gel column chromatography (dichloromethane/methanol 19:1) to thereby obtain 572 mg of compound (IX) (yield 96%).

1-Propylphosphonic acid cyclic anhydride (1 M ethyl acetate solution; 1 ml) was dissolved in acetonitrile (3 ml). Compound (IX) obtained above (596 mg) and triethylamine (0.50 ml) were added thereto. The resultant solution was agitated for 30 minutes at room temperature, followed by addition of hydroxylamine hydrochloride (208 mg). The resultant solution was agitated for 12 hours at room temperature. The reaction mixture was diluted with ethyl acetate, washed with saturated brine and dried over sodium sulfate. Purification by silica gel column chromatography (dichloromethane/methanol 15:1) gave 403 mg of compound (X) (yield 66%).

Compound (IX) (596 mg) or compound (X) (611 mg) obtained above was dissolved in tetrahydrofuran (5 ml). Tetrabutylammonium fluoride (1 M tetrahydrofuran solution, 5 ml) was added thereto. The resultant solution was agitated for 12 hours at room temperature. The reaction mixture was concentrated and then purified by silica gel column chromatography (dichloromethane/methanol 10:1) to thereby obtain respective compounds of interest as a white powder, i.e., (Ie) in 301 mg (yield 82%) and (II) in 309 mg (yield 81%).

Synthesis of 5-O-(3-Carboxypropionyl)Vidarabine and 5-O-(3-(N-Hydroxycarbamoyl)Propionyl)Vidarabine According to a previously disclosed method (Shen, W.; Kim, J.-S.; Kish, P. E.; Zhang, J.; Mitchell, S.; Gentry, B. G;

Breitenbach, J. M.; Drach, J. C.; Hilfinger, J. Bio. Med. Chem. Lett. 2009, 19, 792-796), hydroxyl group of vidarabine manufactured by Tokyo Chemical Industry Co., Ltd. was protected with silyl group. Then, vidarabine was condensed with levulinic acid for esterification. Finally, silyl group was removed to thereby prepare compound (XIII).

Compound (XIII) (463 mg) was dissolved in pyridine (5 ml). Succinic anhydride (120 mg) was added thereto and the solution was agitated for 6 hours at room temperature. Water was added to the reaction mixture. Extraction operation was performed 3 times using dichloromethane. The extracted organic layer was dried over sodium sulfate, followed by filtration. The filtrate was concentrated to obtain a crude product, which was purified by silica gel column chromatography (dichloromethane/methanol 10:1) to thereby obtain 539 mg of compound (XV) (yield 96%).

1-Propylphosphonic acid cyclic anhydride (1 M ethyl acetate solution; 1 ml) was dissolved in acetonitrile (3 ml). Compound (XV) obtained above (564 mg) and triethylamine (0.50 ml) were added thereto. The resultant solution was agitated for 30 minutes at room temperature, followed by addition of hydroxylamine hydrochloride (208 mg). The resultant solution was agitated for 12 hours at room temperature. The reaction solution was diluted with ethyl acetate, washed with saturated brine and dried over sodium sulfate. Purification by silica gel column chromatography (dichloromethane/methanol 10:1) gave 360 mg of compound (XVI) (yield 62%).

Compound (XV) (564 mg) or compound (XVI) (579 mg) obtained above was dissolved in pyridine-acetate buffer, to which hydrazine monohydrate (0.107 ml) was added. The resultant solution was agitated for 1 hour at room temperature. The reaction mixture was concentrated and then purified by silica gel column chromatography (dichloromethane/methanol 10:1) to thereby obtain respective compounds of interest as white powder, i.e., (Ih) in 310 mg (yield 84%) and (Ii) in 305 mg (yield 80%).

<Membrane Adenylyl Cyclase Assay>

Striatal, cardiac and pulmonary tissues were removed from WT (C57BL) (Charles River Laboratories Japan, Inc.) and AC5KO (Circ. Res. 93: 364-371, 2003), both of which were 12-15 weeks of age after birth, and individual membrane protein fractions were prepared therefrom. The resultant membrane preparations were incubated with a reaction mixture (20 mM HEPES, pH 8, 5 mM $MgCl_2$, 0.5 mM EDTA, pH 8, 0.1 mM ATP, 1 mM phospho creatine, 8 U/mL creatine phosphor kinase, 200 μM IBMX) at 30° C. in the presence of forskolin (an activator of adenylyl cyclase) (50 μM, Sigma Cat. No. F6886) and various compounds, to thereby allow production of cAMP. In this assay, striatum- or lung-derived membrane preparations were used in an amount of 1 μg, and heart-derived membrane preparation was used in an amount of 2 μg. 15 minutes (striatum and lung) or 30 minutes (heart) after its start, the reaction was terminated by adding trichloroacetate (TCA) solution to give a final concentration of 5%. Then, the protein was precipitated by centrifugation (13,500× g, 10 min).

<H9c2 Cultured Cells>

Rat heart-derived H9c2 cells (ATCC) were cultured in 10% (v/v) fetal bovine serum (FBS)-containing Dulbecco's Modified Eagle Medium (DMEM, Sigma Cat. No. D6429) in the presence of 95% air+5% $CO_2$ at 37° C. 80-90% confluent H9c2 cells were suspended in 10% FBS-containing DMEM. The cell suspension (500 μl) was added to each well of 24-well plates to give a density of 40,000 cells/well, and incubated overnight at 37° C. Subsequently, cells were incubated in serum-free DMEM (500 μl/well) for 48 hours and subjected to cAMP accumulation assay.

<Rat Adult Cardiac Myocytes>

Sprague-Dawley male rats (Nippon SLC) (240-260 g) were anesthetized with pentobarbital (50 mg/kg ip). After administration of heparin (1000 UPS/kg iv), hearts were removed promptly, and swiftly mounted on a Langendorff apparatus. Perfusion was carried out with a calcium-free Tyrode solution containing 0.06% collagenase and 0.02% protease. Cardiac myocytes liberated into KB solution (KOH 85 mM, KCl 30 mM, $KH_2PO_4$ 30 mM, $MgSO_4$ 3 mM, EGTA 0.5 mM, HEPES 10 mM, 1-Glutamine 50 mM, Taurin 20 mM, pH 7.4) were filtered and suspended in 10% FBS-containing DMEM. The cell suspension (500 μl) was added to each well of 24-well plates to give a density of 40,000 cells/well, and incubated overnight at 37° C. Subsequently, cells were incubated in serum-free DMEM (500 μl/well) for 4 hours and subjected to cAMP accumulation assay (Circulation 98, 1329-1334, 1998).

<cAMP Accumulation Assay>

H9c2 cells were incubated in the presence of 500 μM IBMX for 20 minutes at 37° C. Then, various vidarabine derivatives were added to the culture broth to give a concentration of 50 μM. Cells were further incubated for 10 minutes at 37° C. Subsequently, forskolin was added thereto to give a concentration of 100 μM to thereby start cAMP production reaction. 20 minutes after the start of the reaction, culture broth was suctioned. 7.5% (v/v) TCA solution (200 μl) was added thereto to terminate the reaction. Cells were further incubated at 4° C. overnight. Similar experiments were also carried out on rat adult cultured cardiac myocytes under stimulation with various vidarabine derivatives (10 μM) and forskolin (5 μM).

In both membrane adenylyl cyclase assay and cAMP accumulation assay, the amount of cAMP contained in TCA solution was determined by radioimmunoassay using $[^{25}I]$-cAMP.

<Chronic Catecholamine Loading Experiment>

An osmotic mini-pump filled with isoproterenol was hypodermically implanted in mice, and isoproterenol was administered for 1 week continuously in a sustained-release manner (60 mg/kg). The cardiac function of mice (EF, ejection fraction) was measured by cardiac ultrasonography, and values before and after isoproterenol administration were compared. It is generally known that when isoproterenol is administered to mice with a mini-pump, their cardiac function (EF) decreases (i.e., they manifest heart failure).

<TUNEL Staining of Cardiac Myocytes>

A culture broth of rat embryo cultured cardiac myocytes (pregnant Wistar rats were purchased from Nippon SLC) was stimulated (48 hours) with isoproterenol ($10^{-5}$ M) either alone or in combination with vidarabine, V2E, V3E or V5E ($10^{-5}$ M). Then, apoptosis positive cells were evaluated by TUNEL staining.

<Toxicity Test>

Vidarabine, V2E, V3E and V5E were administered individually to WT (C57BL/6N; Nippon SLC) with an osmotic mini-pump (15 mg/kg/day for 7 days). Then, blood samples were taken and subjected to BUN, creatinine, OPT and GOT measurements. The results were compared with the results from control group.

<TUNEL Staining of Myocardial Tissues>

Apoptosis positive cells of the mice used in the chronic catecholamine loading experiment were evaluated by TUNEL staining.

Results

The newly synthesized three vidarabine derivatives (FIG. 1) were dissolved in pure water to thereby prepare 10 mM stock solutions. Since vidarabine infusion of about 2 mM is used in clinical scenes as an antiherpes therapeutic (Arasena-A for intravenous infusion; Mochida Pharmaceutical Co., Ltd.), it was possible to prepare solutions at concentrations about 5 times higher than that of the infusion. In the present study, vidarabine was dissolved in 100% DMSO to prepare a 10 mM stock solution.

Figure 2:
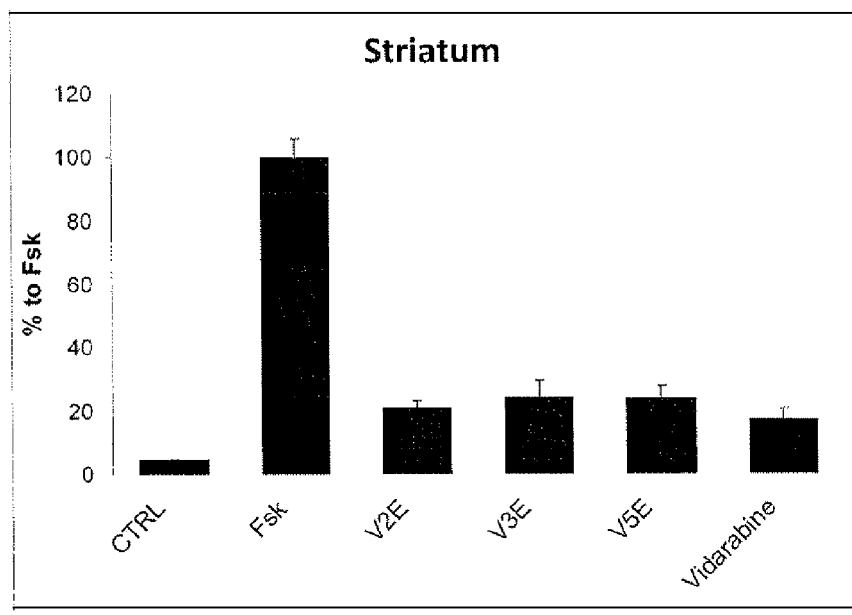
FIG. 2 Inhibitory effects of various compounds on adenylyl cyclase activity in mouse striatum. The striatum is part of the brain. Here, it is known that type 5 adenylyl cyclase occupies almost all of the enzyme activity. For this reason, it is believed that the striatum is more selective than the heart for testing type 5 adenylyl cyclase activity. Relative values are shown with adenylyl cyclase activity in the presence of 50 µM forskolin but in the absence of inhibitors being taken as 100 (n=4, means±S.E.).

Adenylyl cyclase activity in the striatal membrane of WT increased about 15- to 20-fold as a result of stimulation with 50 µM forskolin. When the membrane was treated with various compounds at a concentration of 100 µM, vidarabine, which had been reported as a type 5 selective inhibitor, inhibited adenylyl cyclase activity in the presence of forskolin up to about 17.3%. On the other hand, V2E, V3E and V5E decreased the forskolin-stimulated adenylyl cyclase activity to about 24.5%, about 25.1% and about 24.9%, respectively (FIG. 2).

Figure 3:
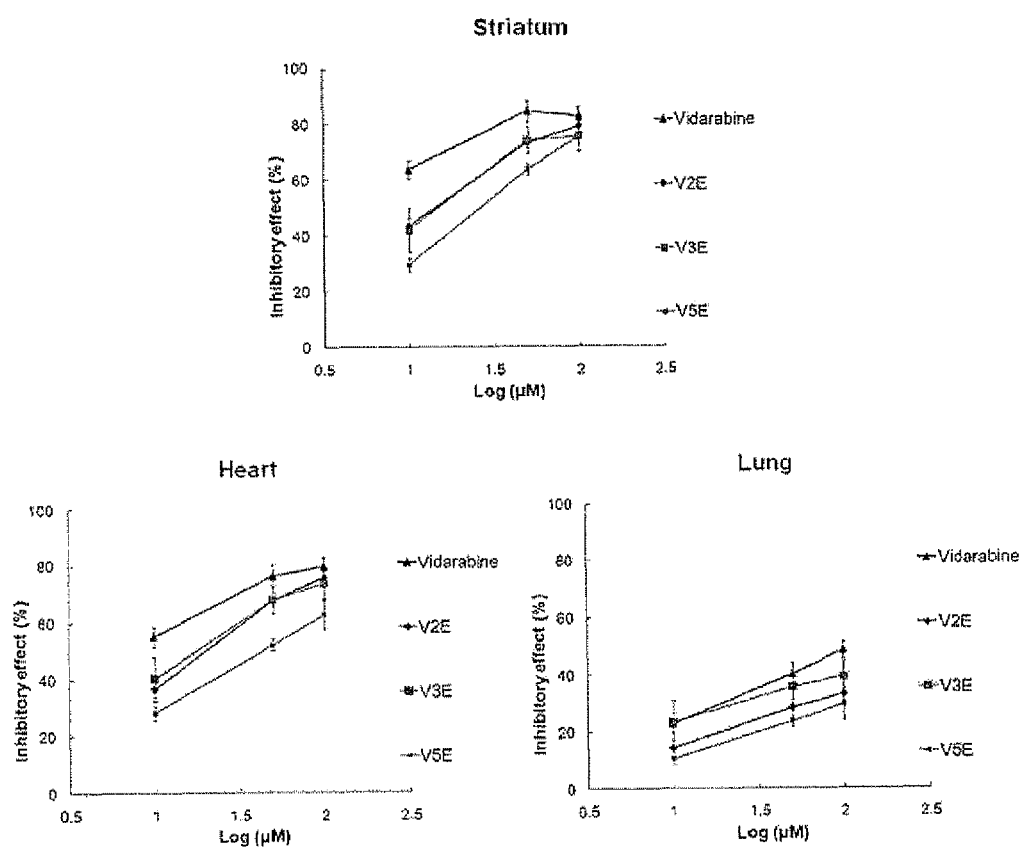
FIG. 3 Inhibitory effects of individual vidarabine derivatives on adenylyl cyclase activity in the striatum, heart and lung. With adenylyl cyclase activity in the presence of 50 forskolin but in the absence of inhibitors being taken as 100, the reductions in adenylyl cyclase activity upon treatment with various inhibitors at the concentrations indicated on the horizontal axis are shown (n=4, means±S.E.).
Figure 4:
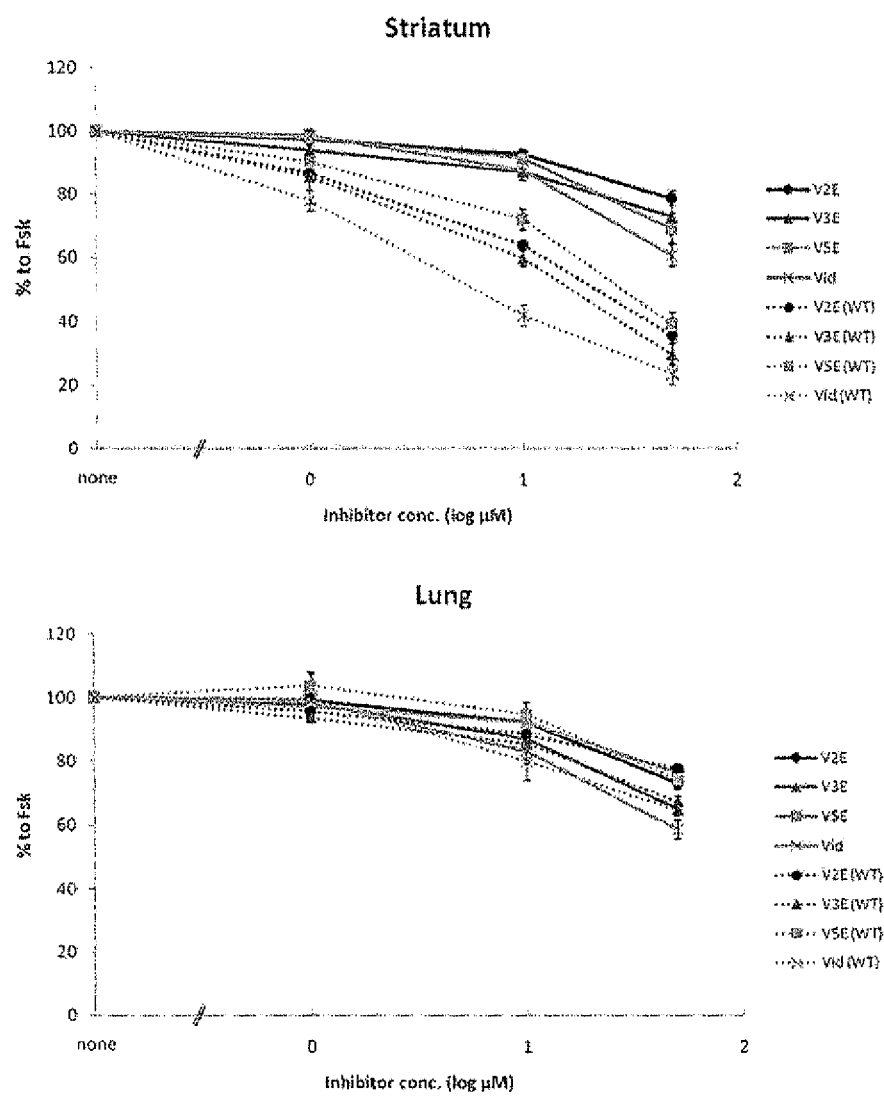
FIG. 4 Inhibitory effects of vidarabine derivatives on adenylyl cyclase activity in individual tissues of wild-type (WT) mice and type 5 adenylyl cyclase knockout (AC5KO) mice. Relative values are shown with adenylyl cyclase activity in the presence of 50 µM forskolin but in the absence of inhibitors being taken as 100 (n=4, means±S.E.).

Subsequently, inhibitory effects of various vidarabine derivatives on adenylyl cyclase activity in the striatum, heart and lung of WT were analyzed at three concentrations (10, 50 and 100 µM). As a result, it was estimated that respective $IC_{50}$ values on adenylyl cyclase activity in the striatum were about 6.0 µM for vidarabine, about 13.1 µM for V2E, about 13.0 µM for V3E and 25.1 µM for V5E. Similarly, respective $IC_{50}$ values of these drugs in the heart were estimated to be 7.7 µM, 17.8 µM, 19.9 µM and 42.9 µM. These results were presumably because the expression ratio of type 5 to the total adenylyl cyclase in the striatum is by far higher than the ratio in the heart (FIG. 3). Further, it was revealed that inhibitory effects of these compounds on adenylyl cyclase activity in the striatum of AC5KO mice were lower than those in the striatum of WT (FIG. 4). In particular, adenylyl cyclase activity in the striatal membrane was retained at about 80% of the control even in the presence of 50 µM inhibitor. This shows that various vidarabine derivatives have a high inhibitory effect on type 5 adenylyl cyclase.

Figure 5:
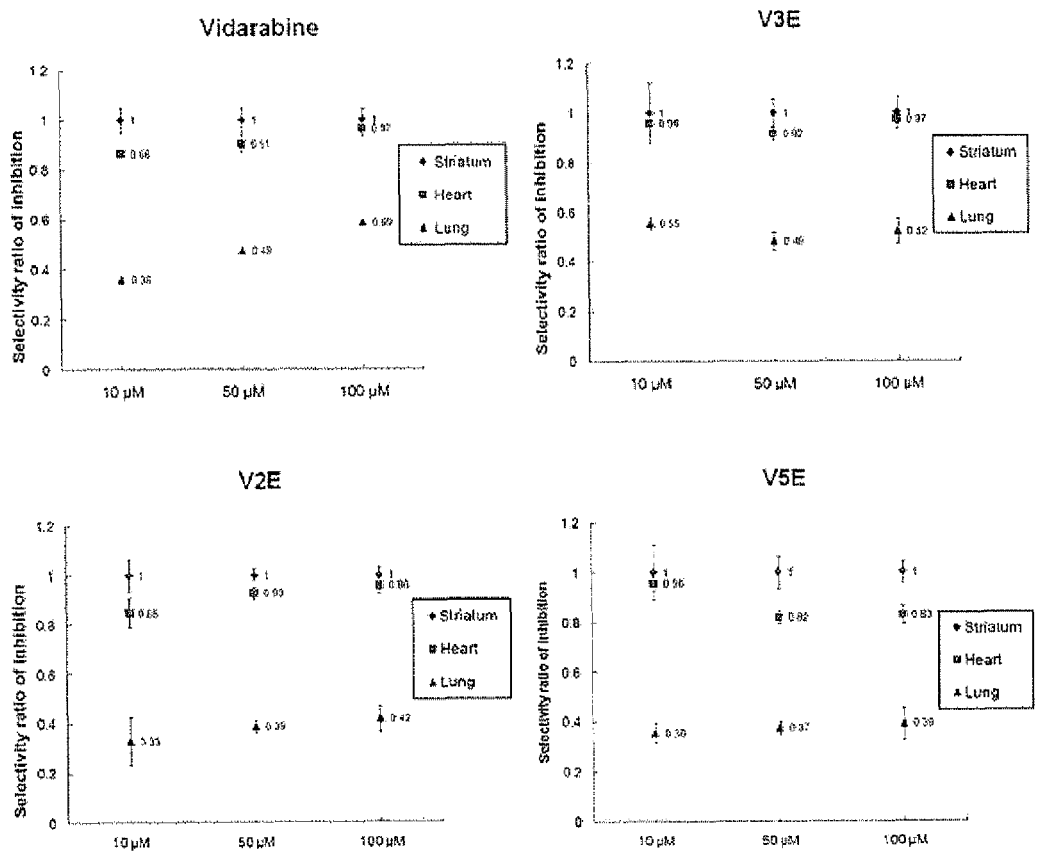
FIG. 5 Tissue selectivity of the inhibitory effects on adenylyl cyclase activity of various vidarabine derivatives. Relative values are shown with the inhibitory effect on striatum adenylyl cyclase activity at each concentration being taken as 1 (n=4, means±S.E.).

Further, at a concentration of 10 µM, V2E inhibited adenylyl cyclase activity in wild-type mouse heart about 2.6 times as strong as in the lung and inhibited adenylyl cyclase activity in WT striatum about 3.0 times as strong as in the lung. The tissue specificity of the inhibitory effect of vidarabine at said concentration is about 2.4-fold higher in the heart than in the lung and about 2.8-fold higher in the striatum than in the lung. Thus, it was suggested that V2E is a highly hydrophilic compound having a type 5-selective inhibitory effect comparable to that of vidarabine (FIG. 5).

Figure 6:
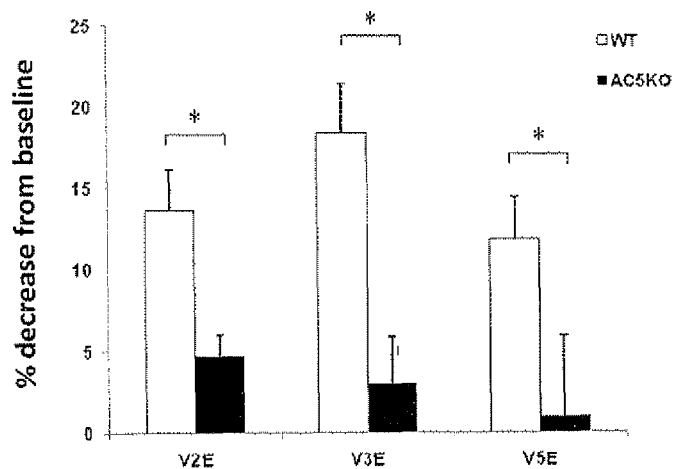
FIG. 6 Inhibitory effects of various compounds on adenylyl cyclase activity in the myocardial tissue membrane preparations of AC5KO and WT hearts. Relative values are shown with adenylyl cyclase activity in the presence of 50 µM isoproterenol but in the absence of inhibitors being taken as 100 (n=8, means±S.E.).

Inhibitory effects of various vidarabine derivatives on AC5KO were compared to their effects on WT. The results revealed that inhibitory effects of various vidarabine derivatives on adenylyl cyclase activity in myocardial tissue membrane protein in WT were significantly higher than in AC5KO. This suggests that vidarabine derivatives have a type 5-selective inhibitory effect (FIG. 6).

Figure 7:
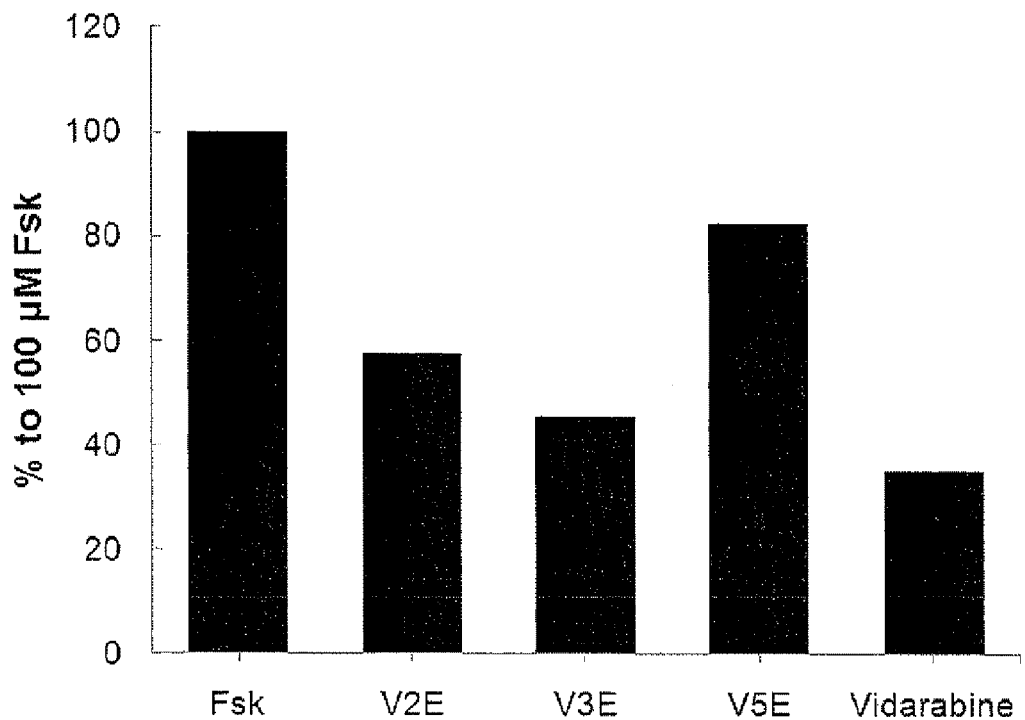
FIG. 7 Effects of various vidarabine derivatives on cAMP accumulation in H9c2 cells caused by forskolin stimulation. Relative values are shown with cAMP level in H9c2 cells in the presence of 100 µM forskolin but in the absence of inhibitors being taken as 100 (n=1).
Figure 8:
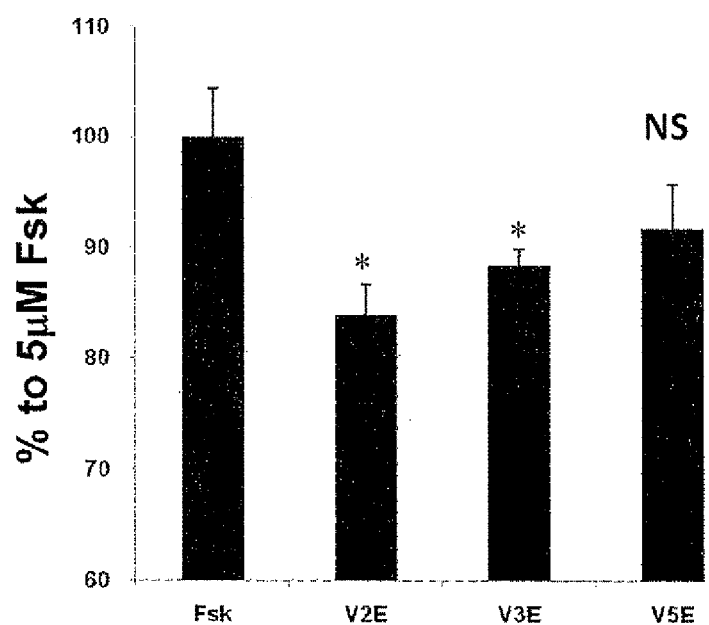
FIG. 8 Effects of various vidarabine derivatives on cAMP accumulation in adult rat cardiac myocytes caused by forskolin stimulation (5 µM). Relative values are shown with cAMP level in adult rat cardiac myocytes in the presence of 5 µM forskolin but in the absence of inhibitors being taken as 100 (n=4, means±S.E.).

On the other hand, for the purpose of examining the presence or absence of inhibitory effect on cAMP production by adenylyl cyclase in intact cells rather than by adenylyl cyclase in membrane samples, the inventors examined the effects of vidarabine derivatives on the level of cAMP accumulating in forskolin-stimulated cells. In this study, a preliminary experiment was conducted using rat heart-derived H9c2 cultured cells as a material. Those cells were selected because some compounds are generally low in cell membrane permeability, and the activity of such compounds in the living body will be extremely low. As a result, in the presence of various inhibitors, the level of cAMP accumulated in response to forskolin showed markedly low values compared to the control (vidarabine: about 35.1%; V2E: about 57.1%; V3E: about 45.7% and V5E: about 82.5%) (FIG. 7). A similar experiment was carried out with adult rat cardiac myocytes. As a result, similar tendencies to those seen in the experiment with H9c2 cells were obtained (FIG. 8). From these results, it was expected that vidarabine and derivatives thereof exert their effect as adenylyl cyclase inhibitor even on intact cells. Briefly, it was found that vidarabine and derivatives thereof have good cell membrane permeability.

Figure 9:
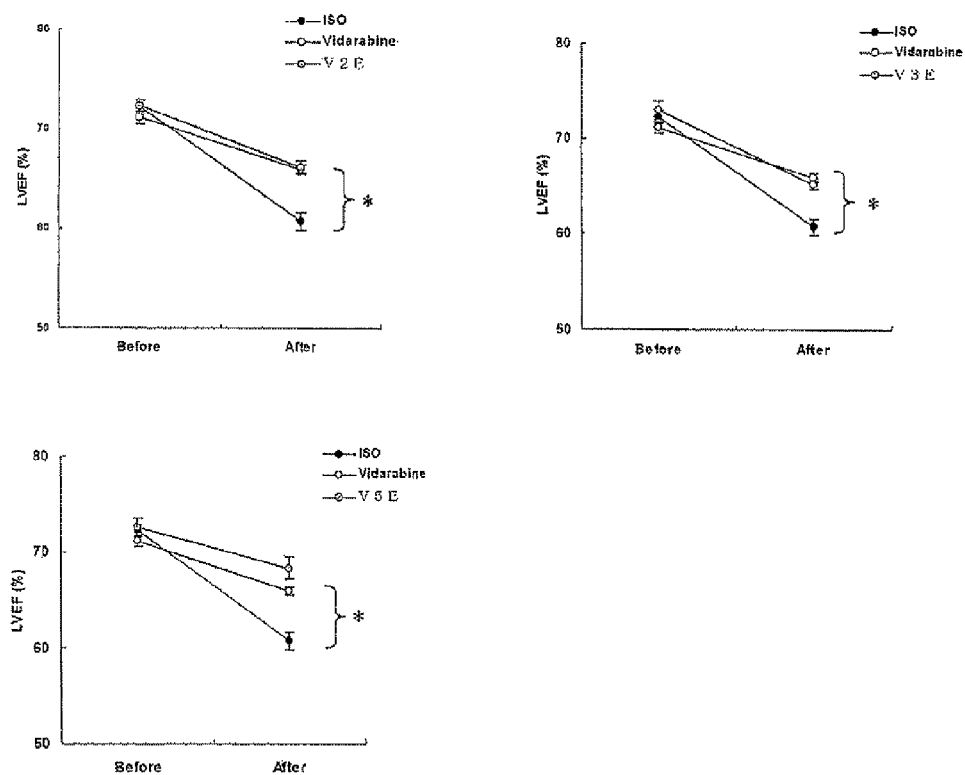
FIG. 9 Prophylactic effects on heart failure. Isoproterenol alone (60 mg/kg/day for 7 days) was administered to wild-type mice (C57BL/6N) for one week with an osmotic mini-pump (Alzet2001) (ISO). Other WT received isoproterenol with vidarabine, V2E, V3E or V5E (15 mg/kg/day for 7 days). The results revealed that the mice which received isoproterenol alone showed decrease in cardiac function (LVEF: cardiac output) compared to the levels before administration whereas in the mice which received isoproterenol and vidarabine simultaneously, the decrease of cardiac function was inhibited significantly. Inhibitory effects on the decrease of cardiac function that were comparable to that of vidarabine were also confirmed in the mice which received isoproterenol in combination with V2E, V3E or V5E (n=3-8, means±SE, *P<0.05).

Isoproterenol alone (60 mg/kg/day for 7 days) was administered to WT (C57BL/6N) for 1 week with an osmotic mini-pump (Alzet 2001). Other WT received isoproterenol and, at the same time, vidarabine, V2E, V3E or V5E (15 mg/kg/day for 7 days). The results revealed that the mice which received isoproterenol alone showed a decrease in cardiac function (LVEF: cardiac output) from the level before administration whereas in the mice which simultaneously received isoproterenol and vidarabine, the decrease of cardiac function was significantly inhibited (FIG. 9). Inhibitory effects on the decrease of cardiac function that were comparable to that of vidarabine were also confirmed in the mice which received isoproterenol in combination with V2E, V3E or V5E (n=3-8, means±SE, *P<0.05) (FIG. 9)

As described so far, it has been revealed in the present study that the newly synthesized three vidarabine derivatives have high hydrophilicity and strongly inhibit type 5 adenylyl cyclase. In particular, it was suggested that the position 2-substituted derivative should have type 5-selective inhibitory effect similar to that of vidarabine, thus indicating the prophylactic effect of the derivative on heart failure.

Figure 10:
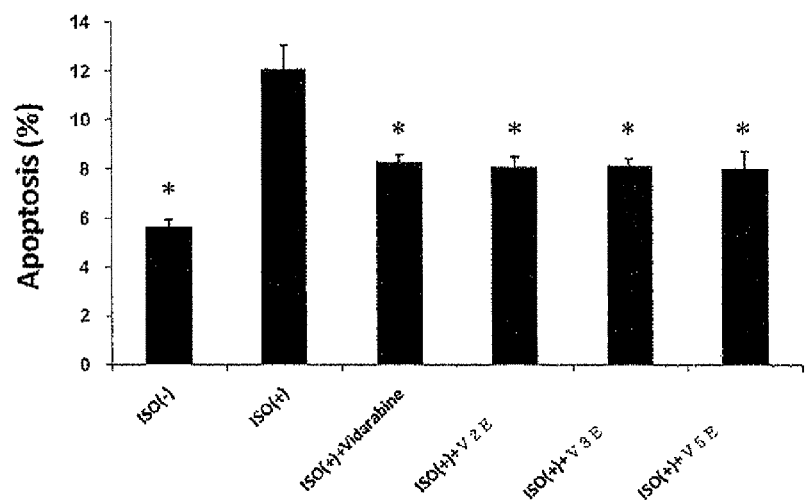
FIG. 10 TUNEL staining of cardiac myocytes. To a culture both of neonatal rat cardiac myocytes, isoproterenol ($10^{-5}$ M) either alone or in combination with vidarabine, V2E, V3E or V5E was added for stimulation (48 hours). Then, apoptosis positive cells were evaluated by TUNEL staining. V2E, V3E and V5E showed inhibitory effects on isoproterenol stimulation-induced apoptosis that were comparable to the effect of vidarabine (n=4-7, means±SE, *P<005).

In TUNEL staining of cardiac myocytes, rat embryo cultured cardiac myocytes were stimulated (48 hours) with isoproterenol ($10^{-5}$ M) either alone or in combination with vidarabine, V2E, V3E or V5E. Then, apoptosis positive cells were evaluated by TUNEL staining. V2E, V3E and V5E showed inhibitory effects on isoproterenol stimulation-induced apoptosis that were comparable to the effect of vidarabine (n=4-7, means±SE, *P<0.05) (FIG. 10).

Figure 11:
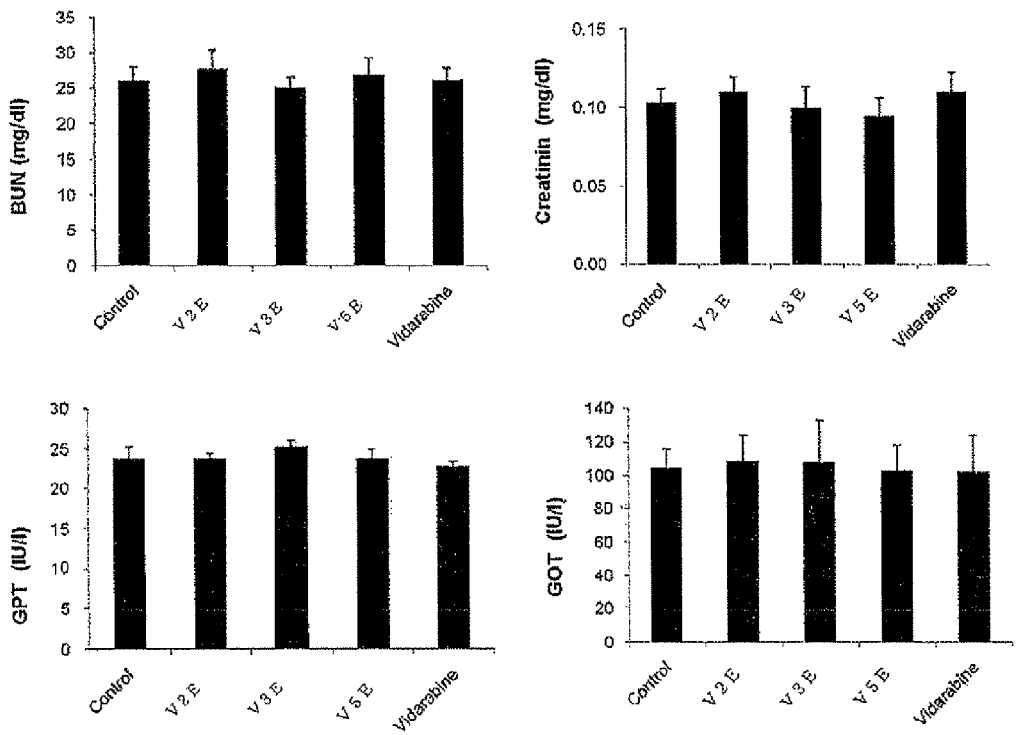
FIG. 11 Toxicity test. Vidarabine, V2E, V3E and V5E were administered individually with an osmotic mini-pump (15 mg/kg/day for 7 days). Then, blood samples were taken and subjected to BUN, creatinine, GPT and GOT measurements. The results were compared with the results from a control group. No significant increase in BUN, creatinine, GPT or GOT was observed (n=4-8, means±SE) in comparison with the control group.

In toxicity test, vidarabine, V2E, V3E and V5E were administered individually with an osmotic mini-pump (15 mg/kg/day for 7 days). Then, blood samples were taken and subjected to BUN, creatinine, OPT and GOT measurements. The results were compared with the results from the control group. No significant increase in BUN, creatinine, OPT or GOT was observed (n=4-8, means±SE) in comparison with the control group (FIG. 11).

Figure 12:
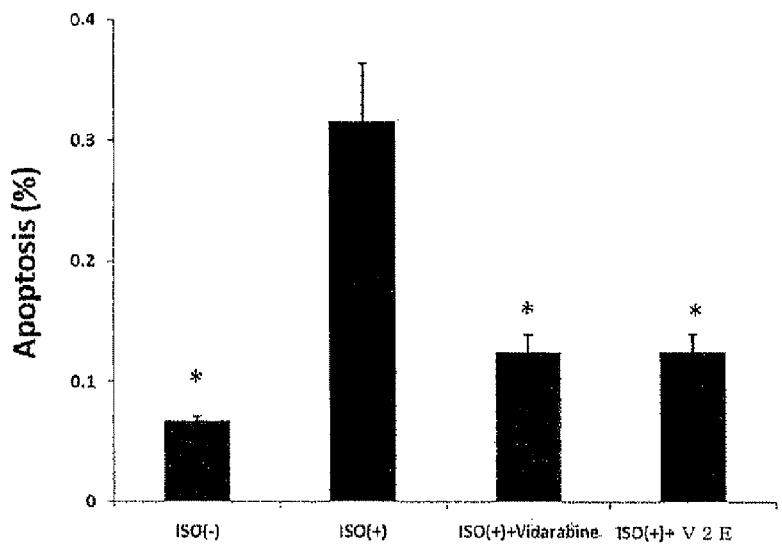
FIG. 12 TUNEL stain of myocardial tissues. Apoptosis positive cardiac myocytes in the hearts of mice used in chronic catecholamine loading experiment (FIG. 9) were evaluated by TUNEL staining (n=4-6, means±SE).

The proportion of apoptosis positive cardiac myocytes in myocardial tissues of chronic catecholamine-loaded mice (prepared with isoproterenol) was evaluated by TUNEL staining. Vidarabine and V2E equally inhibited the apoptosis of cardiac myocytes induced by chronic catecholamine stimulation (n=4-6, means±SE) (FIG. 12).

The migration of vidarabine, V2E, V3E and V5E to the central nervous system was evaluated by antagonism against the tonic extensive convulsion and death initiated in mice by strychnine administration. Strychnine nitrate dissolved in physiological saline was administered in the cervicodorsal hypoderm of mice (C57BL/6N; Nippon SLC; male; 10-12 week old) at a dose of 1.5 mg/kg. Subsequently, the time to death through tonic extensive convulsion was measured. Vidarabine, V2E, V3E and V5E were dissolved or suspended in physiological saline and administered intraperitoneally 15 minutes before strychnine administration.

Figure 13:
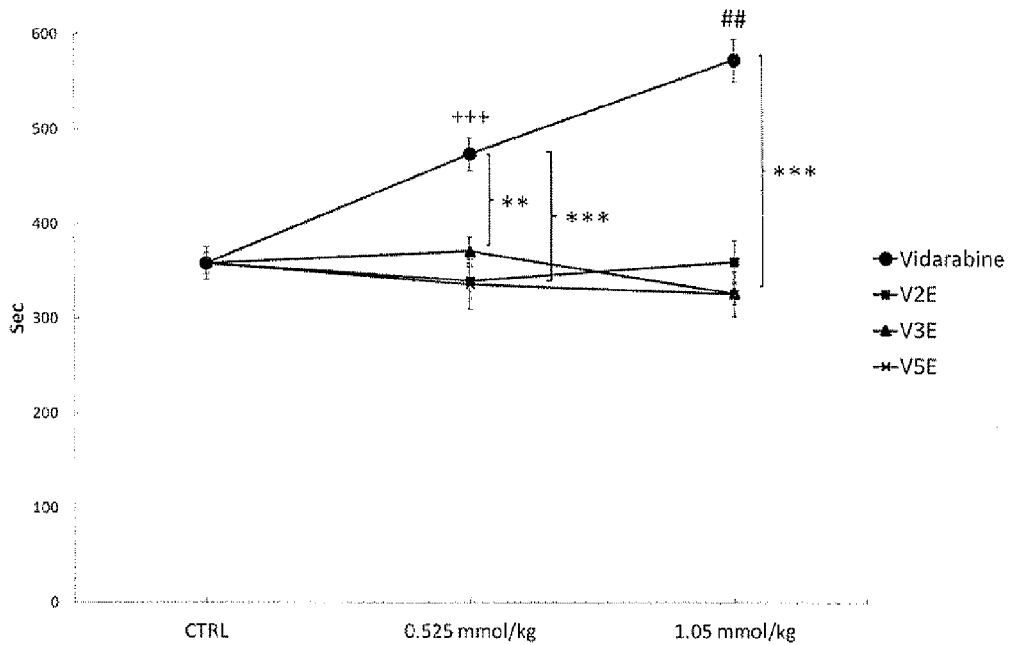
FIG. 13 Effects on the central nervous system. The site of action of those drugs which are reported to have inhibitory action on strychnine convulsion is the central nervous system. Vidarabine also shows migration to the central nervous system and inhibitory action on strychnine convulsion (Pharmaceutical Regulatory Science, 18, 561-576, 1982). Hence, the migration of vidarabine, V2E, V3E and V5E to the central nervous system was evaluated by antagonism against the tonic extensive convulsion and death initiated in WT (C57BL6/N) by strychnine administration. Strychnine nitrate dissolved in physiological saline was administered in the cervicodorsal hypoderm of mice (C57BL/6N; Nippon SLC; male; 10-12 week old) at a dose of 1.5 mg/kg. Subsequently, the time to death through tonic extensive convulsion was measured so that the effect on migration to the central nervous system was evaluated indirectly. Vidarabine, V2E, V3E and V5E were dissolved or suspended in physiological saline and administered intraperitoneally 15 minutes before strychnine administration (n=4-10, means±SE) (FIG. 13). Death was judged to have occurred when the thoracic respiratory movement ceased.

While vidarabine has been applied clinically as a therapeutic for herpetic encephalitis and its migration to the central nervous system has been confirmed, the time to death induced by strychnine convulsion was significantly prolonged by vidarabine in a dose-dependent manner at 150 mg/kg (0.525 mmol/kg) and 300 mg/kg (1.05 mmol/kg). On the other hand, V2E, V3E and V5E did not prolong the time to death at the same dose levels as those of vidarabine. Briefly, none of V2E, V3E and V5E affected the incidence of strychnine-induced death, suggesting the extremely low migration of these drugs to the central nervous system. The mortalilty was 100% in experiments using any of those drugs (n=4-10, means±SE) (FIG. 13).

After mice were inhalationally anesthetized with isoflurane, an electrode catheter (Millar: Model EPR800; size 1.1 F; length 4.5 cm) connected to an electrocardiogram amp for the purpose of recording intracardiac electrocardiogram was slowly inserted through the oral cavity into the esophagus, and fixed at a site where maximum P wave was recorded. The thus fixed electrode catheter was connected to an electrostimulator carefully enough to avoid any movement of its position. Thereafter, body surface electrogram was recorded by II lead. Subsequently, voltage stimuli of 2.5 mA were applied to mice for 60 seconds at intervals of 30 milliseconds to thereby induce transient atrial fibrillation. The time period during which the following phenomena can be confirmed from body surface electrogram was regarded as the duration of atrial P wave disappears from the baseline and the R-R intervals are not regular but produce arrhythmic pulse.

Figure 14:
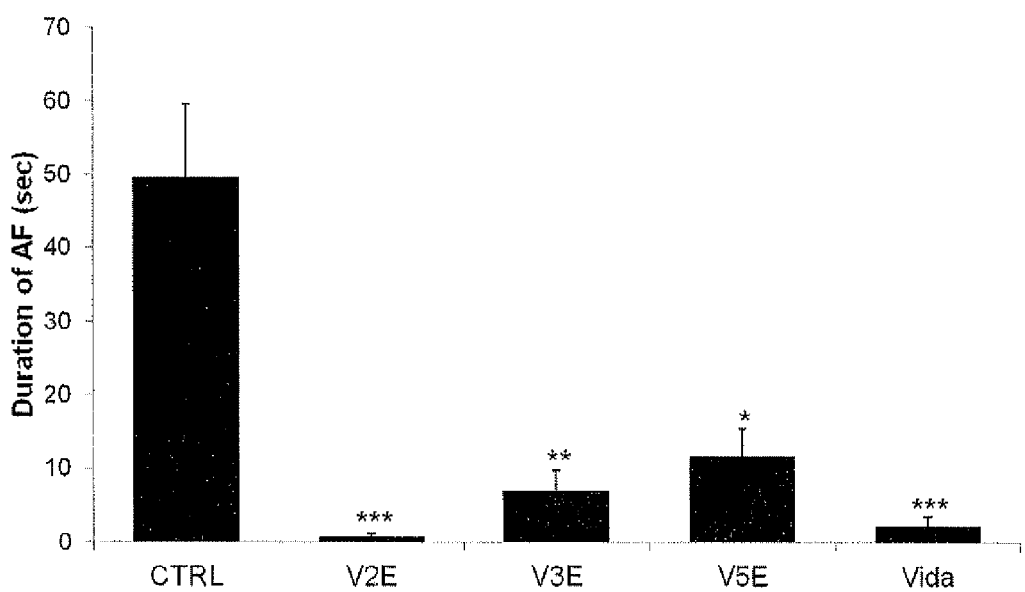
FIG. 14 Antiarrhythmic (atrial fibrillation inhibition) action. To healthy wild type mice (C57BL/6N), vidarabine (15 mg/kg/day), V2E, V3E or V5E (19.8 mg/kg/day) (all of which are dissolved in DMSO) or DMSO alone was administered with an osmotic mini-pump (Alzet 2001). Subsequently, voltage stimuli of 2.5 mA were applied to the mice for 60 seconds at intervals of 30 milliseconds with a transesophageal catheter (atrial tachypacing; Circ Res 97, 62-69, 2005) to induce transient atrial fibrillation. The duration of atrial fibration until the induced transient atrial fibrillation converted to a normal sinus rhythm was measured (n=4-8, means±SE).

To healthy WT (C57BL/6N), each of vidarabine (15 mg/kg/day), V2E, V3E and V5E (19.8 mg/kg/day) (all of which were dissolved in DMSO) or DMSO alone was administered with an osmotic mini-pump (Alzet 2001). Subsequently, atrial fibrillation was induced under the above-described conditions, and the duration of atrial fibrillation until the induced atrial fibrillation converted to a normal sinus rhythm was measured (FIG. 14). This experiment was completed after confirming that the normal sinus rhythm was lasting for at least 5 minutes and that there was no recurrence of atrial fibrillation. For information, the maximum dose of vidarabine approved for use in the treatment of herpes in humans is 15 mg/kg/day for 10 days.

Vidarabine, V2E, V3E and V5E significantly shortened the time for pacing-induced atrial fibrillation to convert to a normal sinus rhythm (n=4-8, means±SE).

All the publications, patents and patent applications cited herein are incorporated herein by reference in their entirety.

INDUSTRIAL APPLICABILITY

The present invention is applicable to prevention and/or treatment of diseases such as heart failure, myocardial infarction and arrhythmia.

The invention claimed is:

1. A compound represented by the following formula (I') or a pharmaceutically acceptable salt, ester or solvate thereof:

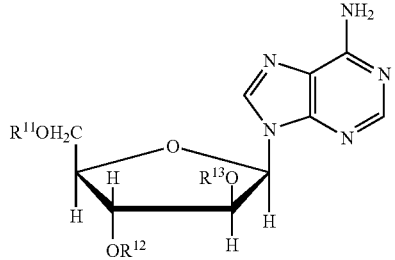

where $R^{11}$, $R^{12}$ and $R^{13}$ each independently represent a hydrogen atom or a group represented by the following formula:

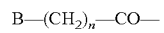

B—(CH$_2$)$_n$—CO— where n represents an integer from 1 to 4 and B is an amino group in which at least one hydrogen atom is substituted with an alkyl group, a carboxyl group or a hydroxycarbamoyl group, provided that all of $R^{11}$, $R^{12}$ and $R^{13}$ are not simultaneously a hydrogen atom, provided that 5'-O-(3-carboxypropanoyl)-9-β-D-arabinofuranosyladenine and 5'-O-(4-carboxybutanoyl)-9-β-D-arabinofuranosyladenine are excluded.

2. The compound according to claim 1, which is represented by any of the following formulas:

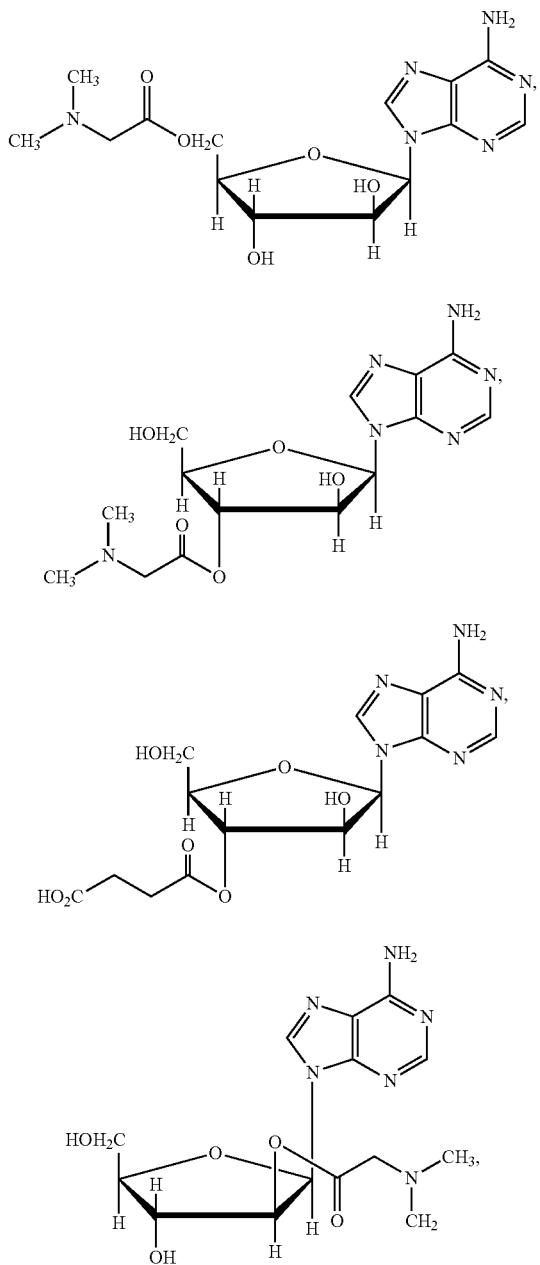

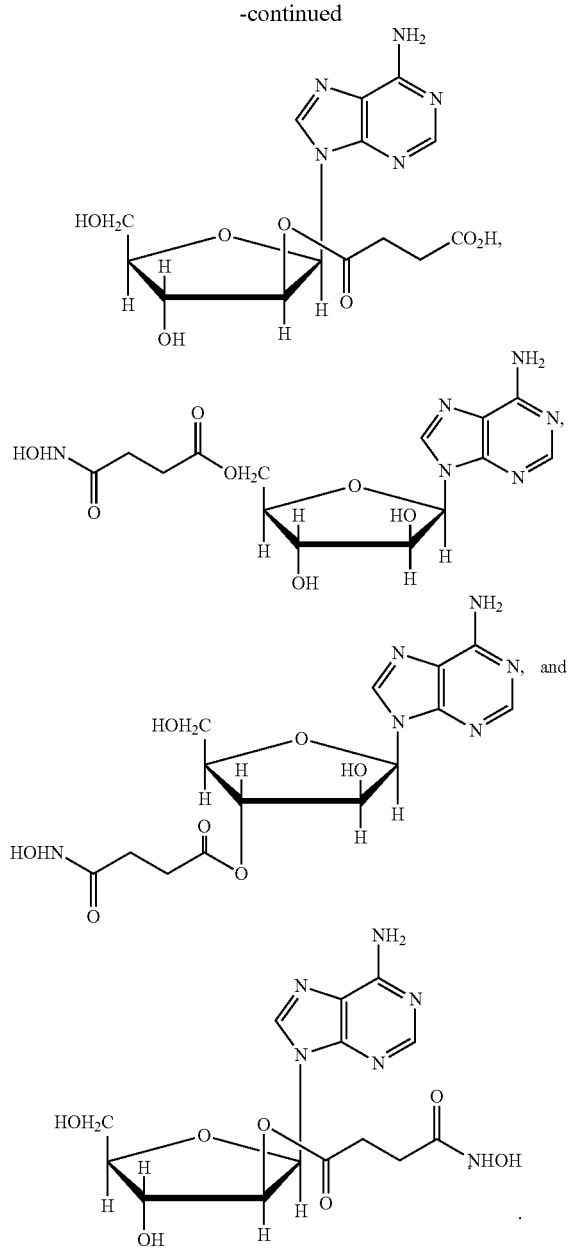

3. A modulator of adenylyl cyclase activity, comprising a compound represented by the following formula (I') or a pharmaceutically acceptable salt, ester or solvate thereof:

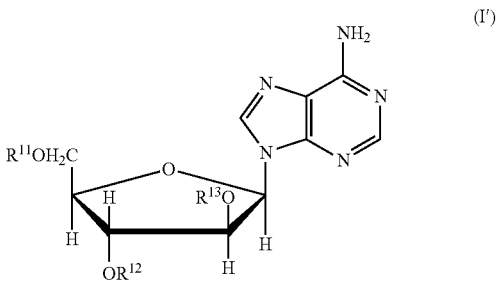

where $R^{11}$, $R^{12}$ and $R^{13}$ each independently represent a hydrogen atom or a group represented by the following formula:

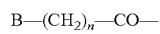

B—(CH$_2$)$_n$—CO— where n represents an integer from 1 to 4 and B is an amino group in which at least one hydrogen atom is substituted with an alkyl group, a carboxyl group or a hydroxycarbamoyl group, provided that all of $R^{11}$, $R^{12}$ and $R^{13}$ are not simultaneously a hydrogen atom.

4. The modulator according to claim 3, wherein the adenylyl cyclase is cardiac adenylyl cyclase.

5. A pharmaceutical composition comprising the compound according to claim 1 or a pharmaceutically acceptable salt, ester or solvate thereof.

6. A food composition comprising the compound according to claim 1 or a pharmaceutically acceptable salt, ester or solvate thereof.

* * * * *

UNITED STATES PATENT AND TRADEMARK OFFICE
CERTIFICATE OF CORRECTION

PATENT NO.         : 9,096,632 B2
APPLICATION NO.    : 13/880346
DATED              : August 4, 2015
INVENTOR(S)        : Ishikawa et al.

It is certified that error appears in the above-identified patent and that said Letters Patent is hereby corrected as shown below:

Title Page Item (73) Assignees

"NATIONAL UNIVERSITY CORPORATION YOKOHAMA NATIONAL UNIVERSITY" should be added.

Signed and Sealed this
Seventeenth Day of May, 2016

Michelle K. Lee
*Director of the United States Patent and Trademark Office*